(12) United States Patent
Feldman et al.

(10) Patent No.: US 8,679,743 B2
(45) Date of Patent: Mar. 25, 2014

(54) REDUCING IRF4, DUSP22, OR FLJ43663 POLYPEPTIDE EXPRESSION

(75) Inventors: Andrew L. Feldman, Rochester, MN (US); Ahmet Dogan, Rochester, MN (US); George Vasmatzis, Oronoco, MN (US); Mark Law, Rochester, MN (US); David I. Smith, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 27 days.

(21) Appl. No.: 13/213,390

(22) Filed: Aug. 19, 2011

(65) Prior Publication Data

US 2011/0306517 A1     Dec. 15, 2011

Related U.S. Application Data

(62) Division of application No. 12/782,484, filed on May 18, 2010, now abandoned.

(60) Provisional application No. 61/179,201, filed on May 18, 2009.

(51) Int. Cl.
*C12Q 1/68* (2006.01)

(52) U.S. Cl.
USPC ............................... 435/6; 435/325; 435/375

(58) Field of Classification Search
None
See application file for complete search history.

(56) References Cited

U.S. PATENT DOCUMENTS

| 2003/0148341 A1 | 8/2003 | Sin et al. |
| 2005/0281743 A1 | 12/2005 | Delaney |
| 2008/0166300 A1 | 7/2008 | Delaney |

OTHER PUBLICATIONS

Feldman et al., "Incidence of TCR and TCL1 Gene Translocations and Isochromosome 7q in Peripheral T-Cell Lymphomas Using Fluorescence In Situ Hybridization," *Am. J. Clin. Pathol.*, 2008, 130:178-185.

Feldman et al., "Overexpression of Syk tyrosine kinase in peripheral T-cell lymphomas," *Leukemia*, 2008, 22:1139-1143.
Feldman et al., "Recurrent translocations involving the IRF4 oncogene locus in peripheral T-cell lymphomas," *Leukemia*, 2009, 23:574-580.
GenBank GI No. 7305518, dated Feb. 19, 2011, 3 pages.
GenBank GI No. 157816962, dated May 15, 2008, 2 pages.
GenBank GI, No. 73992105, dated Aug. 30, 2005, 1 page.
GenBank GI No. 115497401, dated Feb. 10, 2011, 1 page.
GenBank GI No. 194222960, dated Jul. 11, 2008, 1 page.
GenBank GI No. 114605169, dated Sep. 15, 2006, 2 pages.
GenBank GI No. 109069403, dated Jun. 14, 2006, 1 page.
GenBank GI No. 167555103, dated Aug. 3, 2010, 3 pages.
GenBank GI No. 146198766, dated Feb. 11, 2011, 3 pages.
GenBank GI No. 133892215, dated Feb. 11, 2011, 2 pages.
GenBank GI No. 157822426, dated May 14, 2008, 1 page.
GenBank GI No. 229892211, dated Oct. 21, 2009, 1 page.
GenBank GI No. 34147625, dated Dec. 19, 2010, 2 pages.
GenBank GI No. 205277371, dated Oct. 11, 2009, 2 pages.
GenBank GI No. 205277373, dated Oct. 11, 2009, 2 pages.
GenBank GI No. 51094836, dated Aug. 10, 2004, 1 page.
Patterson et al., "Dual-specificity phosphatases: critical regulators with diverse cellular targets," *Biochem. J.*, 2009, 418:475-489.
Schneider et al., "t(3;7)(q27;q32) fuses BCL6 to a non-coding region at FRA7H near miR-29," *Leukemia*, 2008, 22:1262-1266, published online Nov. 8, 2007.
Vasmatzis et al., "Quantitating Tissue Specificity of Human Genes to Facilitate Biomarker Discovery," *Bioinformatics*, 2007, 23:1348-1355.
Wada et al., "IRF4 Translocations are specific for cutaneous anaplastic large cell lymphoma in skin biopsies involved by T-cell lymphoproliferative disorders," *Mod. Pathol.*, 2009, 22 suppl. 1:289A (abst 1308).

*Primary Examiner* — Kimberly Chong
(74) *Attorney, Agent, or Firm* — Fish & Richardson P.C.

(57) ABSTRACT

This document relates to the activity of interferon regulatory factor 4 (IRF4) in T-cell lymphomas. For example, methods and materials involved in reducing the expression of an IRF4 polypeptide in T-cell lymphoma cells and identifying agents having the ability to reduce expression of an IRF4 polypeptide in T-cell lymphoma cells are provided. This document also relates to reducing DUSP22 or FLJ43663 polypeptide activity in T-cell lymphomas. For example, methods and materials involved in reducing the expression of DUSP22 polypeptides and/or FLJ43663 polypeptides in T-cell lymphoma cells and identifying agents having the ability to reduce expression of DUSP22 polypeptides and/or FLJ43663 polypeptides in T-cell lymphoma cells are provided.

3 Claims, 25 Drawing Sheets

SR786  CCRF-CEM
Cell line

SUDHL1  SR786  SeAx
Cell line

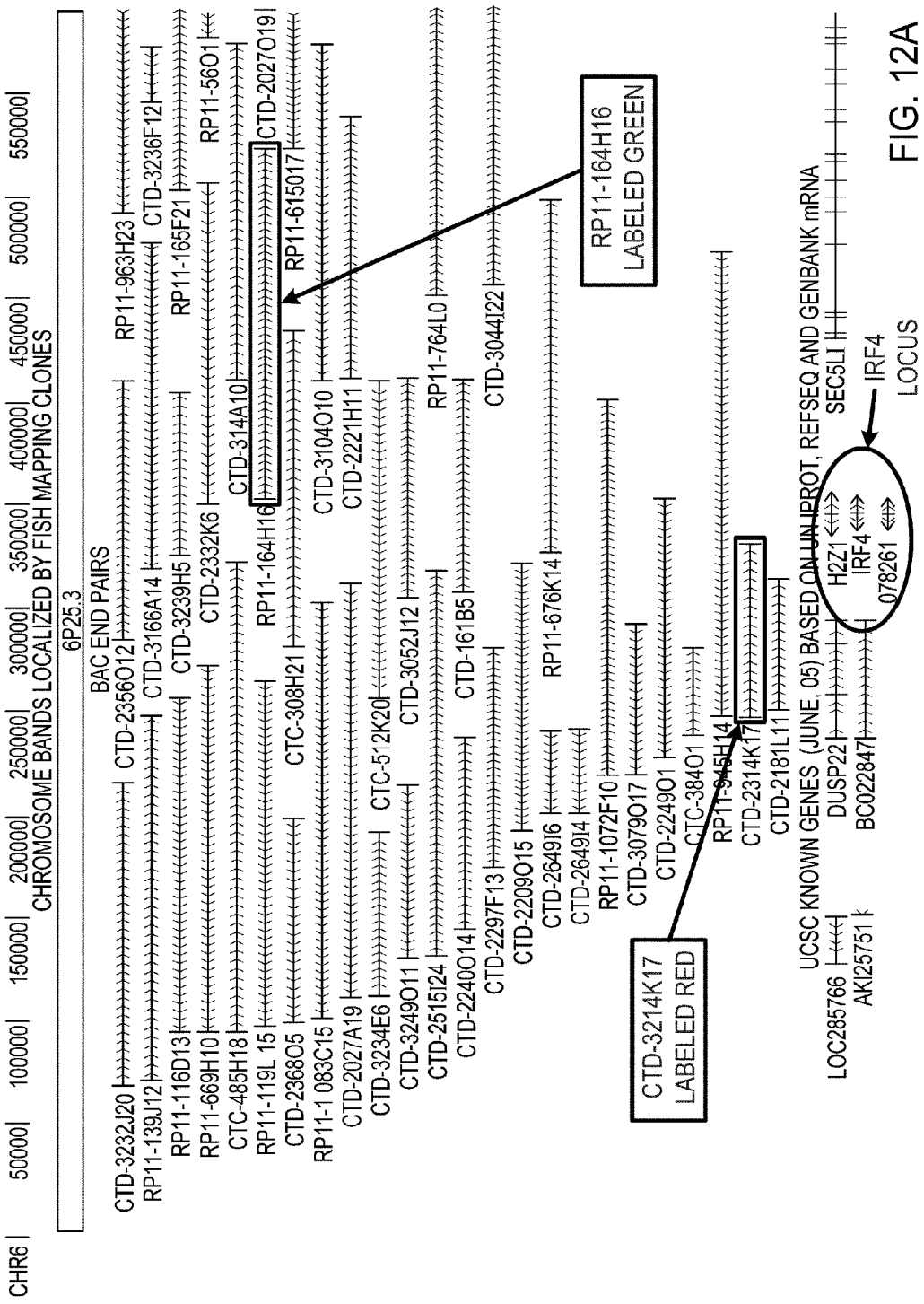

REDUCING IRF4, DUSP22, OR FLJ43663 POLYPEPTIDE EXPRESSION

CROSS-REFERENCE TO RELATED APPLICATIONS

This application is a divisional application of U.S. Ser. No. 12/782,484, filed May 18, 2010, which claims the benefit of U.S. Provisional Application Ser. No. 61/179,201, filed May 18, 2009. The disclosure of the prior applications are considered part of (and are incorporated by reference in) the disclosure of this application.

STATEMENT AS TO FEDERALLY SPONSORED RESEARCH

This invention was made with government support under grant number CA097274 awarded by the National Institutes of Health. The government has certain rights in the invention.

BACKGROUND

1. Technical Field

This document relates to reducing interferon regulatory factor 4 (IRF4) activity in T-cell lymphomas. For example, methods and materials involved in reducing the expression of an IRF4 polypeptide in T-cell lymphoma cells and identifying agents having the ability to reduce expression of an IRF4 polypeptide in T-cell lymphoma cells are provided. This document also relates to reducing DUSP22 or FLJ43663 polypeptide activity in T-cell lymphomas. For example, methods and materials involved in reducing the expression of DUSP22 polypeptides and/or FLJ43663 polypeptides in T-cell lymphoma cells and identifying agents having the ability to reduce expression of DUSP22 polypeptides and/or FLJ43663 polypeptides in T-cell lymphoma cells are provided.

2. Background Information

T-cell lymphomas are aggressive cancers that cause death in the majority of affected patients despite treatment with traditional chemotherapy. Peripheral T-cell lymphomas (PT-CLs), in which abnormal T-lymphocytes are found in the lymph nodes, body organs, and sometimes in the peripheral circulating blood and/or bone marrow, represent 10% of non-Hodgkin lymphomas. PTCLs are fatal in the majority of patients.

SUMMARY

This document relates to reducing interferon regulatory factor 4 (IRF4) activity in T-cell lymphomas. For example, methods and materials involved in reducing the expression of an IRF4 polypeptide in T-cell lymphoma cells and identifying agents having the ability to reduce expression of an IRF4 polypeptide in T-cell lymphoma cells are provided. This document also provides methods and materials for reducing DUSP22 and/or FLJ43663 polypeptide activity in T-cell lymphomas. For example, methods and materials for reducing the expression of DUSP22 polypeptides and/or FLJ43663 polypeptides in T-cell lymphoma cells and identifying agents having the ability to reduce expression of DUSP22 polypeptides and/or FLJ43663 polypeptides in T-cell lymphoma cells are provided.

In some cases, an agent that inhibits the expression of an IRF4 polypeptide can be used to reduce the proliferation of abnormal T-lymphocytes (e.g., T-cell lymphomas). In addition, this document provides methods (e.g., in vivo and in vitro assays) for identifying agents (e.g., antibodies, siRNAs, or other compounds) that can reduce the expression of an IRF4 polypeptide in a mammal.

In some cases, an agent that inhibits the expression of an DUSP22 polypeptide and/or an FLJ43663 polypeptide can be used to reduce the proliferation of abnormal T-lymphocytes (e.g., T-cell lymphomas). In addition, this document provides methods (e.g., in vivo and in vitro assays) for identifying agents (e.g., antibodies, siRNAs, or other compounds) that can reduce the expression of an DUSP22 polypeptide and/or an FLJ43663 polypeptide in a mammal.

In general, one aspect of this document features a method for reducing IRF4 polypeptide expression within a T-cell lymphoma cell. The method comprises, or consists essentially of, identifying a mammal having a T-cell lymphoma cell and administering an IRF4 polypeptide inhibitor to the mammal under conditions wherein the IRF4 polypeptide expression is reduced. The mammal can be a human. The cell can be a peripheral T-cell lymphoma cell. The peripheral T-cell lymphoma cell can be a primary cutaneous type anaplastic large cell lymphoma cell. The administering step can include intravenous administration. The IRF4 polypeptide inhibitor can be an siRNA molecule capable of inducing RNA interference against mRNA encoding an IRF4 polypeptide.

In another aspect, this document features a method for reducing DUSP22 polypeptide expression within a T-cell lymphoma cell. The method comprises, or consists essentially of, (a) identifying a mammal having a T-cell lymphoma cell, and (b) administering an DUSP22 polypeptide inhibitor to the mammal under conditions wherein the DUSP22 polypeptide expression is reduced. The mammal can be a human. The T-cell lymphoma cell can be a peripheral T-cell lymphoma cell. The peripheral T-cell lymphoma cell can be a primary cutaneous type anaplastic large cell lymphoma cell. The administering step can comprise intravenous administration. The DUSP22 polypeptide inhibitor can be an siRNA molecule capable of inducing RNA interference against mRNA encoding an DUSP22 polypeptide.

In another aspect, this document features a method for reducing FLJ43663 polypeptide expression within a T-cell lymphoma cell. The method comprises, or consists essentially of, (a) identifying a mammal having a T-cell lymphoma cell, and (b) administering an FLJ43663 polypeptide inhibitor to the mammal under conditions wherein the FLJ43663 polypeptide expression is reduced. The mammal can be a human. The T-cell lymphoma cell can be a peripheral T-cell lymphoma cell. The peripheral T-cell lymphoma cell can be a primary cutaneous type anaplastic large cell lymphoma cell. The administering step can comprise intravenous administration. The FLJ43663 polypeptide inhibitor can be an siRNA molecule capable of inducing RNA interference against mRNA encoding an FLJ43663 polypeptide.

In another aspect, this document features a method for assessing a lymphoma of a mammal. The method comprises, or consists essentially of, (a) detecting an IRF4 translocation within the lymphoma, and (b) classifying the mammal as having cutaneous anaplastic large-cell lymphoma. The mammal can be a human.

In another aspect, this document features a method for assessing a lymphoma of a mammal. The method comprises, or consists essentially of, (a) determining whether or not the lymphoma of the mammal has a translocation selected from the group consisting of IRF4 translocations, DUSP22 translocations, and FLJ43663 translocations, (b) classifying the mammal as having an anaplastic large-cell lymphoma if the lymphoma has the translocation. The mammal can be a human.

In another aspect, this document features a method for assessing a lymphoma of a mammal. The method comprises, or consists essentially of, (a) determining whether or not the a cell of the lymphoma expresses an elevated level of an FLJ43663 mRNA or polypeptide, and (b) classifying the mammal as having an anaplastic large-cell lymphoma if the cell expresses the elevated level. The mammal can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
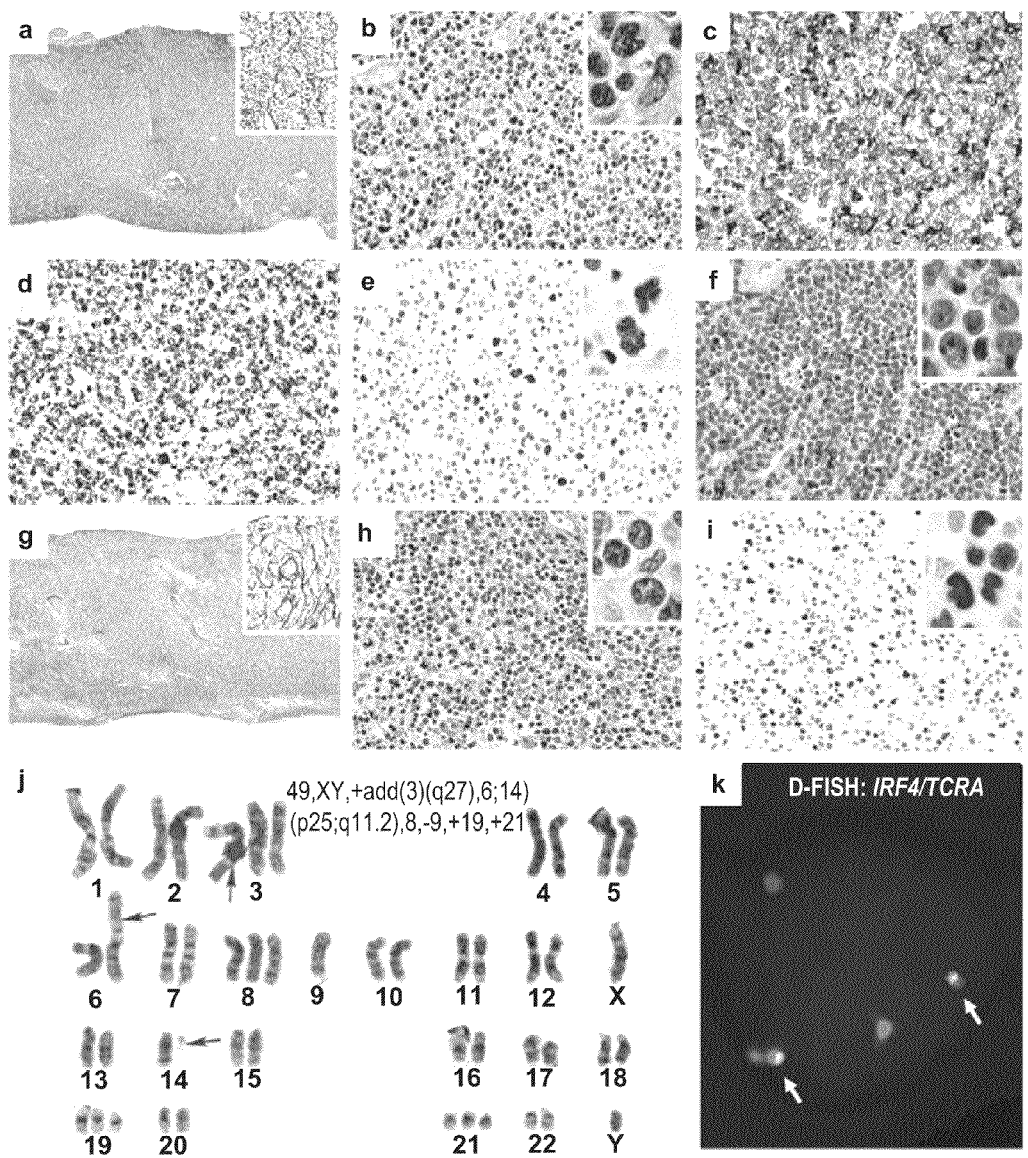
FIG. 1 shows photographs of immunohistochemistry, karyotype, and fluorescence in situ hybridization (FISH) identifying peripheral T-cell lymphomas, unspecified (PTCL-Us) with IRF4/TCRA translocations involving bone marrow and skin: (a) Diffuse infiltration of bone marrow (75% involvement) in a 67 year-old male (Case 1; H&E, ×4) (reticulin fibrosis is present (inset, ×40)); (b) Medium to large tumor cells with plasma cells in the background (H&E, ×40; inset, ×100); Tumor cells are positive for (c) CD3, (d) TIA1, (e) and IRF4 (×40; inset, ×100); (f) Skin biopsy from the same patient 4 months later (H&E, ×40; inset, ×100)); (g) Diffuse infiltration of bone marrow (40% involvement) in a 71 year-old male (Case 2; H&E, ×4; reticulin, inset, ×40); (h) Mostly medium-sized tumor cells with plasma cells in the background (H&E, ×40; inset, ×100); (i) Tumor cells are positive for IRF4 (×40; inset, ×100); (j) Karyotype shows t(6; 14)(p25; q11.2); (k) Dual-fusion fluorescence in situ hybridization (D-FISH) shows IRF4/TCRA fusion signals (arrows).

This document relates to reducing IRF4 polypeptide activity, DUSP22 polypeptide activity, and/or FLJ43663 polypeptide activity in T-cell lymphomas. For example, methods and materials are provided for reducing the expression of an IRF4 polypeptide in T-cell lymphoma cells and identifying agents having the ability to reduce expression of an IRF4 polypeptide in T-cell lymphoma cells. IRF4 polypeptides can be expressed in the cells of any mammal (e.g., a mouse, (GI: 7305518), rat (GI:157816962), dog (GI:73992105), cow (GI: 115497401), horse (GI:194222960), chimpanzee (GI: 114605169), monkey (GI:109069403), and human (GI: 167555103)). DUSP22 polypeptides can be expressed in the cells of any mammal (e.g., a mouse (GI: 146198766 for isoform A and 133892215 for isoform B), rat (GI: 157822426), chimpanzee (GI: 229892211), and human (GI: 34147625)). FLJ43663 polypeptides can be expressed in the cells of any mammal (e.g., a human (GI: 205277371, 205277373, or 51094836)). An agent to reduce the expression of an IRF4 polypeptide, a DUSP22 polypeptide, and/or FLJ43663 polypeptide can be administered to a mammal. A mammal can be any type of mammal including, without limitation, a mouse, rat, dog, cat, horse, sheep, goat, cow, pig, monkey, or human.

In some cases, an agent to reduce the expression of an IRF4 polypeptide, a DUSP22 polypeptide, and/or FLJ43663 polypeptide can be administered to a mammal that has been identified as having a peripheral T-cell lymphoma. Peripheral T-cell lymphomas can include: anaplastic large cell lymphoma, primary systemic type; anaplastic large cell lymphoma, primary cutaneous type; angioimmunoblastic T-cell lymphoma; T-cell prolymphocytic leukemia; T-cell large granular lymphocytic leukemia; adult T-cell leukemia/lymphoma; enteropathy-associated T-cell lymphoma; hepatosplenic T-cell lymphoma; Mycosis fungoides/Sezary syndrome; subcutaneous panniculitis-like T-cell lymphoma; and unspecified type peripheral T-cell lymphomas. An inhibitor of an IRF4 polypeptide can be any agent that reduces the expression of an IRF4 polypeptide (e.g., an siRNA molecule, antisense oligonucleotide, or peptide nucleic acid) or that reduces the activity of an IRF4 polypeptide (e.g., an inhibitory anti-IRF4 antibody, anti-IRF4 aptamer, or an IRF4 polypeptide antagonist). In some cases, the methods and materials provided herein can be used to treat a mammal that has a T-cell lymphoma by reducing IRF4 polypeptide expression, thereby reducing the level of T-cell lymphoma cell proliferation, or increasing the level of T-cell lymphoma cell apoptosis. An inhibitor of an DUSP22 polypeptide can be any agent that reduces the expression of an DUSP22 polypeptide (e.g., an siRNA molecule, antisense oligonucleotide, or peptide nucleic acid) or that reduces the activity of an DUSP22 polypeptide (e.g., an inhibitory anti-DUSP22 antibody, anti-DUSP22 aptamer, or an DUSP22 polypeptide antagonist). In some cases, the methods and materials provided herein can be used to treat a mammal that has a T-cell lymphoma by reducing DUSP22 polypeptide expression, thereby reducing the level of T-cell lymphoma cell proliferation, or increasing the level of T-cell lymphoma cell apoptosis. An inhibitor of an FLJ43663 polypeptide can be any agent that reduces the expression of an FLJ43663 polypeptide (e.g., an siRNA molecule, antisense oligonucleotide, or peptide nucleic acid) or that reduces the activity of an FLJ43663 polypeptide (e.g., an inhibitory anti-FLJ43663 antibody, anti-FLJ43663 aptamer, or an FLJ43663 polypeptide antagonist). In some cases, the methods and materials provided herein can be used to treat a mammal that has a T-cell lymphoma by reducing FLJ43663 polypeptide expression, thereby reducing the level of T-cell lymphoma cell proliferation, or increasing the level of T-cell lymphoma cell apoptosis.

This document provides nucleic acid molecules that can reduce the expression of an IRF4 polypeptide, a DUSP22 polypeptide, and/or FLJ43663 polypeptide. For example, antisense oligonucleotides, siRNA molecules, and other nucleic acid constructs encoding transcription or translation products can be used to reduce the expression of an IRF4 polypeptide, a DUSP22 polypeptide, and/or FLJ43663 polypeptide. The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acid molecules that are present in a naturally occurring genome, including nucleic acids that normally flank one or both sides of the nucleic acid in a naturally occurring genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

A nucleic acid construct can comprise a vector containing a nucleotide sequence encoding a transcription or translation product targeting the expression of an IRF4 polypeptide, a DUSP22 polypeptide, and/or FLJ43663 polypeptide with any desired transcriptional and/or translational regulatory sequences, such as promoters, UTRs, and 3' end termination sequences. For example, a polyadenylation region at the 3'-end of the coding region can be included for expression of a polypeptide. In some cases, the polyadenylation region can be derived from a natural gene. Vectors can also include origins of replication, scaffold attachment regions (SARs), markers, homologous sequences, and introns, for example. The vector may also comprise a marker gene that confers a selectable phenotype on cells. The marker may encode antibiotic resistance, such as resistance to kanamycin, G418, bleomycin, hygromycin.

In some cases, an siRNA molecule, an antisense nucleic acid, or an interfering RNA for reducing the expression of an IRF4 polypeptide can be similar or identical to part of an IRF4 allele in a mammal. In some cases, an siRNA molecule, an antisense nucleic acid, or an interfering RNA for reducing the expression of an DUSP22 polypeptide can be similar or identical to part of a DUSP22 allele in a mammal. In some cases, an siRNA molecule, an antisense nucleic acid, or an interfering RNA for reducing the expression of an FLJ43663 polypeptide can be similar or identical to part of an FLJ43663 allele in a mammal. Antisense nucleic acids or interfering RNAs can be about 10 nucleotides to about 2,500 nucleotides in length. For example, nucleic acids described herein can be used as an antisense nucleic acid to an IRF4 allele. In some cases, the transcription product of a nucleic acid described herein can be similar or identical to the sense coding sequence of an IRF4 allele, but is an RNA that is unpolyadenylated, lacks a 5' cap structure, or contains an unsplicable intron.

In some cases, a nucleic acid can have catalytic activity such as a DNA enzyme. For example, a 10-23 DNAzyme can have a cation-dependent catalytic core of 15 deoxyribonucleotides that bind to and cleave target RNA (e.g., an IRF4 RNA, a DUSP22 RNA, and/or an FLJ43663 RNA) between an unpaired purine and paired pyrimidine through a de-esterification reaction. The catalytic core can be flanked by complementary binding arms of 6 to 12 nucleotides in length that confer specificity to an IRF4 mRNA molecule, a DUSP22 mRNA molecule, or an FLJ43663 mRNA molecule.

In some cases, a nucleic acid can be transcribed into a ribozyme that affects expression of an IRF4 mRNA, a DUSP22 mRNA, or FLJ43663 mRNA. Heterologous nucleic acids can encode ribozymes designed to cleave IRF4 mRNA transcripts, thereby preventing expression of an IRF4 polypeptide. Heterologous nucleic acids can encode ribozymes designed to cleave DUSP22 mRNA transcripts, thereby preventing expression of an DUSP22 polypeptide. Heterologous nucleic acids can encode ribozymes designed to cleave FLJ43663 mRNA transcripts, thereby preventing expression of an FLJ43663 polypeptide. Various ribozymes can cleave mRNA at site-specific recognition sequences. For example, hammerhead ribozymes with flanking regions that form complementary base pairs with an IRF4 mRNA can be used to reduce expression of an IRF4 polypeptide by cleaving IRF4 mRNAs at locations containing a 5'-UG-3' nucleotide sequence.

A nucleic acid described herein can be transcribed into an RNA that is capable of inducing an RNA interference response. In some cases, an interfering RNA can anneal to itself to form, for example, a double stranded RNA having a stem-loop structure. One strand of the stem portion of a double stranded RNA can comprise a sequence that is similar or identical to the sense coding sequence of an IRF4 polypeptide (or a DUSP22 polypeptide or FLJ43663 polypeptide) and that is about 10 nucleotides to about 2,500 nucleotides in length. In some cases, the length of the nucleic acid sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA can comprise an antisense sequence of an IRF4 polypeptide (or a DUSP22 polypeptide or FLJ43663 polypeptide) and can have a length that is shorter, the same as, or longer than the length of the corresponding sense sequence. The loop portion of a double stranded RNA can be from 10 nucleotides to 500 nucleotides in length, for example from 15 nucleotides to 100 nucleotides, from 20 nucleotides to 300 nucleotides or from 25 nucleotides to 400 nucleotides in length. In some cases, the loop portion of the RNA can include an intron.

A nucleic acid can be adapted to facilitate efficient entry into cells. For example, a nucleic acid can be conjugated to and/or complexed with a delivery reagent (e.g., cationic liposomes). In some cases, a conjugate or complex can include a ligand of a T-cell surface receptor. In some cases, a nucleic acid can be complexed or conjugated to a protein to confer increased cellular uptake and increased nuclease resistance of oligonucleotides (e.g., Atelocollagen).

An inhibitor (e.g., a treatment agent) of an IRF4 polypeptide, of a DUSP22 polypeptide, or of an FLJ43663 polypeptide can be administered to a mammal alone or in combination with other agents (e.g., another inhibitor of an IRF4 polypeptide or other chemotherapy agents). For example, a composition containing an IRF4 siRNA can be administered alone or in combination with chemotherapy agents (e.g., cytotoxic agents, proteosome inhibitors, histone deacetylase inhibitors, and/or mTOR inhibitors) to a mammal identified as having a T-cell lymphoma. In some cases, a composition containing an IRF4 siRNA can be administered in combination with a composition containing an DUSP22 siRNA and/or an FLJ43663 siRNA. Such a composition can contain additional ingredients including, without limitation, pharmaceutically acceptable vehicles. A pharmaceutically acceptable vehicle can be, for example, saline, water, lactic acid, or mannitol.

A composition containing an inhibitor of an IRF4 polypeptide, a DUSP22 polypeptide, or an FLJ43663 polypeptide can be administered to a mammal by any appropriate route, such as enterally (e.g., orally), parenterally (e.g., subcutaneously, intravenously, intradermally, intramuscularly, or intraperitoneally), intracerebrally (e.g., intraventricularly, intrathecally, or intracisternally) or intranasally (e.g., by intranasal inhalation).

Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets can be coated by methods known in the art. Preparations for oral administration can also be formulated to give controlled release of the agent.

Intranasal preparations can be presented in a liquid form (e.g., nasal drops or aerosols) or as a dry product (e.g., a powder). Both liquid and dry nasal preparations can be administered using a suitable inhalation device. Nebulized aqueous suspensions or solutions can also be prepared with or without a suitable pH and/or tonicity adjustment.

A composition containing an inhibitor of an IRF4 polypeptide, a DUSP22 polypeptide, or an FLJ43663 polypeptide can be administered to a mammal in any amount, at any frequency, and for any duration effective to achieve a desired outcome (e.g., reduce expression of an IRF4 polypeptide, a DUSP22 polypeptide, or an FLJ43663 polypeptide). In some cases, a composition containing an agent that reduces the expression of an IRF4 polypeptide, a DUSP22 polypeptide, or an FLJ43663 polypeptide can be administered to a mammal to reduce an IRF4 polypeptide, a DUSP22 polypeptide, or an FLJ43663 polypeptide expression in a mammal by 1, 5, 10, 11, 12, 13, 14, 15, 16, 17, 18, 19, 20, 25, 30, 35, 40, 45, 50, 55, 60, 65, 70 percent or more). An effective amount of an agent that reduces the expression of an IRF4 polypeptide, a DUSP22 polypeptide, or an FLJ43663 polypeptide can be any amount that reduces IRF4 polypeptide, DUSP22 polypeptide, or FLJ43663 polypeptide expression without producing significant toxicity to a mammal. In some cases, an effective amount of an agent that reduces the expression of an IRF4 polypeptide, a DUSP22 polypeptide, or an FLJ43663 polypeptide can be between 1 µg and 500 mg (e.g., between 1 µg and 250 mg, between 1 µg and 200 mg, between 1 µg and 150 mg, between 1 µg and 100 mg, between 1 µg and 50 mg, between 1 µg and 10 mg, between 1 µg and 1 mg, between 1 µg and 100 µg, between 1 µg and 50 µg, between 5 µg and 100 mg, between 10 µg and 100 mg, between 100 µg and 100 mg, or between 10 µg and 10 mg). Various factors can influence the actual effective amount used for a particular application. For example, the frequency of administration, duration of treatment, use of multiple treatment agents, route of administration, and level of expression of an IRF4 polypeptide, a DUSP22 polypeptide, or an FLJ43663 polypeptide may require an increase or decrease in the actual effective amount administered.

The frequency of administration of an agent that reduces the expression of an IRF4 polypeptide, a DUSP22 polypeptide, or an FLJ43663 polypeptide can be any frequency that reduces the expression of an IRF4 polypeptide, a DUSP22 polypeptide, or an FLJ43663 polypeptide without producing significant toxicity to the mammal. For example, the frequency of administration can be from about three times a day to about twice a month, or from about once a week to about once a month, or from about once every other day to about once a week, or from about once a month to twice a year, or from about four times a year to once every five years, or from about once a year to once in a lifetime. The frequency of administration can remain constant or can be variable during the duration of treatment. For example, an agent that reduces the expression of an IRF4 polypeptide, a DUSP22 polypeptide, or an FLJ43663 polypeptide can be administered daily, twice a day, five days a week, or three days a week. An agent that reduces the expression of an IRF4 polypeptide, a DUSP22 polypeptide, or an FLJ43663 polypeptide can be administered for five days, 10 days, three weeks, four weeks, eight weeks, 48 weeks, one year, 18 months, two years, three years, or five years. A course of treatment can include rest periods. For example, an agent that reduces the expression of an IRF4 polypeptide, a DUSP22 polypeptide, or an FLJ43663 polypeptide can be administered for five days followed by a rest period (e.g., 1, 2, 3, 4, 5, 7, 14, 30, 60 or 90 days) and such a regimen can be repeated multiple times. As with the effective amount, various factors can influence the actual frequency of administration used for a particular application. For example, the effective amount, duration of treatment, use of multiple treatment agents, route of administration, and level of expression of an IRF4 polypeptide, a DUSP22 polypeptide, or an FLJ43663 polypeptide may require an increase or decrease in administration frequency.

An effective duration for administering an agent that reduces the expression of an IRF4 polypeptide, a DUSP22 polypeptide, or an FLJ43663 polypeptide can be any duration that reduces the number of abnormal T-lymphocytes in a mammal without producing significant toxicity to the mammal. Thus, the effective duration can vary from several days to several weeks, months, or years. In general, the effective duration for reducing the expression of an IRF4 polypeptide, a DUSP22 polypeptide, or an FLJ43663 polypeptide can range in duration from several days to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and level of expression of an IRF4 polypeptide, a DUSP22 polypeptide, or an FLJ43663 polypeptide.

The term "decreased level" as used herein with respect to the level of an IRF4 polypeptide, a DUSP22 polypeptide, or an FLJ43663 polypeptide, or activity of an IRF4 polypeptide (e.g., to bind DNA and activate transcription of target genes), a DUSP22 polypeptide, or an FLJ43663 polypeptide is any level that is below a median IRF4 polypeptide, DUSP22 polypeptide, or FLJ43663 polypeptide level in a tissue sample from a random population of mammals (e.g., a random population of 10, 20, 30, 40, 50, 100, or 500 mammals) that have a peripheral T-cell lymphoma. In some cases, a sample of T-cell lymphoma cells can have a 20%, 30%, 40%, or 50% decrease in the level of an IRF4 polypeptide, a DUSP22 polypeptide, or an FLJ43663 polypeptide following treatment with an agent that reduces the expression of an IRF4 polypeptide, a DUSP22 polypeptide, or an FLJ43663 polypeptide.

In some cases, a decreased level of IRF4 polypeptide, DUSP22 polypeptide, or FLJ43663 polypeptide expression can be determined by assaying T-cell proliferation, apoptosis, or cell cycle phase. For example, a decreased level of an IRF4 polypeptide can result in a 10%, 20%, or 30% reduction in T-cell proliferation following treatment with an agent that reduces the expression of an IRF4 polypeptide. In some cases, a decreased level of an IRF4 polypeptide can result in a 10%, 20%, or 30% increase in the number of T-cell lymphoma cells undergoing apoptosis after treatment with an IRF4 polypeptide inhibitor. In some cases, a decreased level of an IRF4 polypeptide can result in a 10%, 20%, or 30% increase in the level of T-cell lymphoma cells in the G0/G1 cell cycle phase and a 10%, 20%, or 30% decrease in the level of S-phase T-cell lymphoma cells after treatment with an IRF4 polypeptide inhibitor.

In addition, this document provides methods for identifying treatment agents that can reduce the expression of an IRF4 polypeptide, a DUSP22 polypeptide, or an FLJ43663 polypeptide from among various test and candidate agents. Treatment agents that can inhibit expression of an IRF4 polypeptide, a DUSP22 polypeptide, or an FLJ43663 polypeptide in cells can be identified by screening test agents and candidate agents (e.g., from synthetic compound libraries and/or natural product libraries). Test agents and candidate agents can be obtained from any commercial source and can be chemically synthesized. Test agents and candidate agents can be screened and can be characterized using in vitro cell-based assays, cell free assays, and/or in vivo animal models. In some cases, a candidate agent can be identified from among test agents any appropriate assay to determine whether or not a test agent reduces the expression of an IRF4 polypeptide, a DUSP22 polypeptide, or an FLJ43663 polypeptide.

For example, primary tissue, cell lines, or animal models can be used to identify test agents that reduce the expression of an IRF4 polypeptide, a DUSP22 polypeptide, or an FLJ43663 polypeptide. In some cases, blood samples can be obtained from anonymous healthy donors and T-cells isolated and purified. In vitro assays can be performed using IRF4-positive T-cell lymphoma cell lines such as Karpas 299, SR786, SeAx, MyLa, and Hut78. In some cases, IRF4 expression can be induced in normal T-cells by culturing in the presence of phytohemagglutinin (e.g., 2.5 µg/ml). Animal models (e.g., IRF4 knockout mice) or cell lines (e.g., IRF4-negative Jurkat cells) can be used as controls for confirming the ability of a test agent or candidate agent to reduce the expression of an IRF4 polypeptide in vivo.

Any appropriate assay can be used to identify test agent that are capable of reducing the expression of an IRF4 polypeptide, a DUSP22 polypeptide, or an FLJ43663 polypeptide. For example, reduction of IRF4, DUSP22, or FLJ43663 expression can be determined by western blot or quantitative real-time PCR. In some cases, reduction of an IRF4 polypeptide, a DUSP22 polypeptide, or an FLJ43663 polypeptide can be determined by an IRF4, DUSP22, or FLJ43663 activity assay. For example, the level of IRF4 expression can be determined by assessing T-cell proliferation (e.g., measuring tritiated-thymidine ($H^3$-TdR) or carboxyfluorescein succinimidyl ester (CFSE)), determining cell cycle phase (e.g., using flow cytometric analysis after treatment with five-bromo-2-deoxyuridine (BrU) to distinguish between G0/G1, S, G2/M), or assaying for apoptosis (e.g., flow cytometric analysis after Annexin-V-fluoroscein isothiocyanate (FITC) and propidium iodide (PI) staining). In some cases, reduction of IRF4 expression can be determined by assays directed towards transcriptional targets of an IRF4 polypeptide (e.g., MYC (myc proto-oncogene protein), PRDM1 (PR domain-containing protein 1), CDK6 (cyclin-dependent kinase 6), VEGFA (vascular endothelial growth factor A), IL-2 (interleukin-2), IL-4 (interleukin-4), BCL2 (B-cell lymphoma protein 2), GATA3 (GATA-binding factor 3), and/or CCNB (Cyclin B1) polypeptides). For example, a reduction in the expression of an IRF4 polypeptide can be identified by a western blot or quantitative real-time PCR results demonstrating a decreased level of MYC polypeptide. Assays can be performed at any time following introduction of a test, candidate, or treatment agent (e.g., about one, two, three, four, and/or six days after administration of an IRF4 polypeptide inhibitor).

This document also provides a massively parallel sequencing of mate-pair DNA libraries that can be used to detect chromosomal translocations in, for example, lymphomas. Recent technologic advances in massively parallel ("Next Generation") DNA sequencing offer a new tool for detecting genetic abnormalities in diseased human tissues. However, high cost, bioinformatic challenges, and analysis time can preclude whole genome sequencing for clinical and most investigational applications. The advantages of the approach described herein are the ability to detect all translocations regardless of the formation of fusion transcripts, and a dramatic reduction in time and resources by reducing the amount of sequenced DNA by a factor of about 200 compared to whole genome sequencing.

In some cases, a clinical test can include obtaining nucleic acid (e.g., genomic DNA) from a mammal, creating a mate-pair DNA library, performing nucleic acid sequencing (e.g., massively parallel "Next Generation" DNA sequencing), and mapping the sequence data to a reference genome using an algorithm (e.g., an algorithm described herein and elsewhere (Vasmatzis et al., *Bioinformatics*, 23:1348-1355 (2007))). Such a clinical test can be used to identify patients with any particular chromosomal translocation or set of chromosomal translocations located across a mammal's genome.

One identified biomarker that can be used as described herein includes a translocation of DUSP22 and FLJ43663. About half of ALCLs lack ALK translocations, and this ALK-negative subset has a poorer prognosis than ALK-positive ALCLs. The advantage to utilizing biomarkers discovered as a result of the approach described herein is their applicability to TCLs (and especially ALCLs) that lack ALK expression. These biomarkers include DUSP22 and FLJ43663. These biomarkers can be used for diagnostic/prognostic purposes.

This document also provides methods and materials for reducing the expression of DUSP22 or FLJ43663 to treat patients with TCLs. Inhibiting or reducing expression of DUSP22 and/or FJL43663 can be used as a treatment for patients with TCLs. The current method of treating TCL consists of a chemotherapeutic regimen, usually "CHOP" or minor variations on this regimen. This is a non-targeted regimen, i.e. it kills dividing cells, whether cancerous or not, and thus has significant toxicity. Furthermore, despite such treatment, the majority of patients die of their disease. One example of the strategy described herein is that of inhibiting DUSP22. Such a strategy is a targeted strategy, i.e. it is directed at a polypeptide whose importance was demonstrated specifically in TCL cells. Another advantage of a targeted strategy over conventional chemotherapy is that measurement of the targeted polypeptide can be used as a biomarker to predict response. Thus, in the example of DUSP22 inhibition, this treatment can be used only in patients whose tumors express DUSP22 polypeptides, allowing therapy to be "individualized" to those most likely to benefit.

As described herein, the presence of translocations involving IRF4, DUSP22, and/or FLJ43663 can indicate that a mammal (e.g., human) has a TCL or a particular type of TCL (e.g., anaplastic large-cell lymphoma). For example, the presence of an IRF4 translocation in a lymphoma sample from a human can indicate that that human has cutaneous anaplastic large-cell lymphoma. In some cases, the presence of a translocation involving IRF4, DUSP22, and/or FLJ43663 can indicate that the mammal (e.g., human) has an anaplastic large-cell lymphoma.

As also described herein, the expression of FLJ43663 (e.g., FLJ43663 mRNA or polypeptide) can indicate that a mammal (e.g., human) has an anaplastic large-cell lymphoma. Any appropriate method can be used to assess cells for the expression of FLJ43663 mRNA or polypeptide. For example, RT-PCR can be used to assess FLJ43663 mRNA levels, and immuno-based assays can be used to assess FLJ43663 polypeptide levels.

This document also provides antibodies (e.g., monoclonal, polyclonal, or fragments thereof) having the ability to bind (e.g., specifically bind) an FLJ43663 polypeptide. Such antibodies can be generated against an amino acid sequence (e.g., 20, 25, 30, 40, 50-mer, or more) encoded by the last 1737 nucleotides of the sequence set forth in GenBank GI No. 205277371 or against the amino acid sequence (e.g., 20, 25, 30, 40, 50-mer, or more) set forth in GenBank GI No. 51094836.

The invention will be further described in the following examples, which do not limit the scope of the invention described in the claims.

EXAMPLES

Example 1

Recurrent Translocations Involving the IRF4 Oncogene in Peripheral T-Cell Lymphomas Specimens from 169 patients with primary T-cell lymphomas (PTCL) diagnosed by WHO criteria were studied. There were 104 males and 65 females (M:F ratio, 1.6:1). The mean age was 58 years (range, 5-92 years). Cases included 23 angioimmunoblastic T-cell lymphomas (AITLs, 13%), 72 PTCL-unspecified (43%), 18 ALK-positive anaplastic large-cell lymphomas (ALCLs) (11%), 24 ALK-negative ALCLs (14%), 14 C-ALCLs (8%), and 18 other PTCLs (Table 1).

TABLE 1

IRF4 Translocations and IRF4 Protein Expression in Peripheral T-cell Lymphomas

| Diagnosis | FISH # pos.* | FISH % | Immunohistochemistry # pos.* | Immunohistochemistry % |
|---|---|---|---|---|
| Angioimmunoblastic T-cell lymphoma | 0/19 | 0 | 0/23 | 0 |
| PTCL, unspecified | 3/64 | 5 | 20/72 | 28 |
| (CD30-positive) | (1/17) | (6) | (13/18) | (72) |
| (CD30-negative) | (2/47) | (4) | (7/54) | (13) |
| Anaplastic large cell lymphoma, ALK-positive | 0/18 | 0 | 16/17 | 94 |
| Anaplastic large cell lymphoma, ALK-negative | 1/23 | 4 | 20/22 | 91 |
| Cutaneous anaplastic large cell lymphoma | 8/14 | 57 | 13/14 | 93 |
| T-cell large granular lymphocyte leukemia | 0/4 | 0 | 0/4 | 0 |
| Hepatosplenic T-cell lymphoma | 0/3 | 0 | 0/3 | 0 |
| Subcutaneous panniculitis-like T-cell lymphoma | — | — | 0/1 | 0 |
| Enteropathy-associated T-cell lymphoma | 0/2 | 0 | 0/2 | 0 |
| Extranodal NK/T-cell lymphoma, nasal type | 0/8 | 0 | 0/8 | 0 |
| Total | 12/155 | 8 | 69/166 | 42 |

*Includes informative cases only, of 169 total cases tested.

Fluorescence In Situ Hybridization (FISH)

Breakapart and dual fusion IRF4 and TCRA FISH probes were developed. BAC clones (Table 2) were identified using the University of California Santa Cruz Genome Browser (located on the World Wide Web at www.genome.UCSC.edu) and ordered from ResGen™ Invitrogen (Carlsbad, Calif.). Positive cases were confirmed using a second breakapart IRF4 probe (probe #2, Table 1). BAC DNA was isolated using the Qiagen (Valencia, Calif.) Plasmid Maxi Kit and fluorescently labeled using SpectrumOrange-dUTP or SpectrumGreen-dUTP and the Abbott Molecular (Des Plaines, Ill.) Nick Translation Kit. Centromeric and telomeric BAC DNA was labeled with different fluorophores for breakapart probes, and with the same fluorophore for dual-fusion (D-FISH) probes. Specificity of hybridization was confirmed on metaphases from a splenic marginal zone lymphoma with IRF4/IGH fusion, a PTCL with a TCRA translocation, and normal samples. TCRB and TCRG probes were purchased from Dako (Carpinteria, Calif.). The upper limit of the normal range for each probe was determined using a 95% confidence interval. Upper limits of normal for IRF4, TCRA, TCRB, and TCRG were 6%, 9%, 5%, and 6%, respectively.

TABLE 2

BAC Clones Used to Prepare Fluorescence In Situ Hydridization Probes

| Locus | Centromeric (BAC Clones) | Telomeric (BAC Clones) |
|---|---|---|
| IRF4 (6p25) [probe #1] | RP11-164H16 | CTD-2314K17 |
| | | RP11-119L15 |
| IRF4 (6p25) [probe #2] | RP11-164H16 | CTD-2308G5 |
| RCRA (14q11) | RP11-524O1 | CTD-2555K7 |
| | RP11-689J19 | RP11-137H15 |
| | RP11-702N19 | RP11-298I3 |
| | CTD-2574K8 | |

Paraffin tissue microarrays (TMAs) were constructed. In cases with insufficient tissue, whole-tissue sections were analyzed. B5- and formalin-fixed cases were included. Sections were sequentially immersed in Citrisolve, Lugol solution, and sodium thiocyanate. Slides were microwaved for 5 minutes in citrate buffer, then digested in 0.4% pepsin solution at 37° C. Ten microliters of FISH reagent (7 μL LSI buffer and 3 μl probe) were placed on each slide and slides were coverslipped, denatured, and incubated in a humidified chamber at 37° C. for 12 hours. Slides were washed, counterstained with 4',6-diamidino-2-phenylindole dihydrochloride, and analyzed by a microscopist (ML) using a fluorescent microscope with appropriate filter sets. A minimum of 50 cells and a maximum of 200 cells were scored per case. A minimum of 20 abnormal cells were required for a sample to be considered abnormal. Some cases were non-informative due to hybridization failures. Positive cases detected on TMAs were confirmed on whole tissue sections. Scoring for IRF4 in four translocated cases with areas showing confluent sheets of tumor cells areas revealed a mean of 71% positive cells (range, 55%-93%).

Immunohistochemistry (IHC)

Five-micron paraffin whole-tissue sections were immunostained using antibodies to assist in disease classification. For IRF4 immunostaining, whole-tissue or TMA sections were pretreated in 1 mM EDTA buffer at pH 8.0 for 30 minutes at 98° C. (PT Module, Lab Vision, Fremont, Calif.), then stained for IRF4 using a monoclonal mouse anti-human antibody (MUM1p, 1:50; Dako). Detection was carried out on a Dual Link Envision+/DAB+ (Dako). Scoring was performed in correlation with H&E and appropriate immunostains (e.g., CD20 and CD3). Specimens were considered positive for IRF4 when >30% of tumor cells demonstrated nuclear staining. Technical factors precluded scoring in rare cases. Diagnosis of C-ALCL required CD30 positivity in >75% of tumor cells, as per WHO criteria. This cutoff also was used to define CD30 positivity in cases of PTCL-U.

Conventional Cytogenetics

Results of karyotype analysis prepared at the time of biopsy were reviewed retrospectively when available.

Results

Twelve PTCLs with IRF4 translocations among 155 PTCLs with informative FISH results (8%; Tables 1, 3). These included 3/64 PTCL-Us (5%), 1/23 ALK-negative ALCLs (4%), and 8/14 C-ALCLs (57%) were identified. IRF4 translocations were not seen in ALK-positive ALCLs, AITLs, or other PTCL subtypes. An IRF4 polypeptide was detected in the majority of ALCLs, regardless of type (Table 1). Staining for IRF4 was positive in 72% of CD30-positive PTCL-Us and 13% of CD30-negative PTCL-Us, and was negative in other PTCL subtypes. All cases with IRF4 translocations were positive for IRF4 by IHC.

TABLE 3

Peripheral T-cell lymphomas with IRF4 Translocations

| Case | Age/Sex | Diagnosis | Site | Time from diagnosis (mos) | Cytotoxic phenotype* | IRF4 FISH | IRF4/TCRA Fusion | Karyotype | Treatment | Follow-up |
|---|---|---|---|---|---|---|---|---|---|---|
| 1 | 67/M | PTCL-U | BM | — | YES | — | — | 48-49, XY, +3[5], +5, der(6)t(6; 14)(p25; q11.2), add(7)(p11.2), −14, +16, +16[5], −20, −22[4], +1, −2mar[cp6]/95-98, idemx2, +3-8mar[2] | CHOP, ICE, ITMTX | alive, progressive cutaneous disease, 4 mos |
| | | | skin | 2 | YES | — | — | — | | |
| | | | skin | 4 | — | POS | POS | — | | |
| 2 | 71/M | PTCL-U | BM | — | YES | POS | POS | 49, XY, +add(3)(q27), t(6; 14)(p25; q11.2), +8, −9, +19, +21† | — | — |
| 3 | 48/F | Cutaneous ALCL | skin | — | — | — | — | — | PUVA, IFNα-2A, CHOP | alive, in remission, 154 mos |
| | | | skin | 1 | — | — | — | — | | |
| | | | skin | 83 | YES | POS | NEG | — | | |
| | | | LN | 126 | — | POS | — | — | | |
| | | | LN | 134 | — | POS | NEG | — | | |
| 4 | 67/M | Cutaneous ALCL | skin | — | — | — | — | — | — | alive, LN involvement, 7 mos |
| | | | LN | 7 | NO | POS | NEG | — | | |
| 5 | 89/F | Cutaneous ALCL | skin | — | NO | POS | NEG | — | XRT, CHOP | died, progressive cutaneous disease, no autopsy, 4 mos |
| 6 | 65/M | Cutaneous ALCL | skin | — | YES | POS | NEG | — | CHOP | alive, skin recurrence, 27 mos |
| 7 | 52/M | Cutaneous ALCL | skin | — | — | POS | NEG | — | CHOP | died, unrelated cause, no autopsy, 9 mos |
| | | | LN | 1 | NO | — | — | — | | |
| 8 | 74/M | Cutaneous ALCL | skin | — | NO | — | — | — | — | alive, LN involvement, 34 mos |
| | | | LN | 34 | NO | POS | NEG | — | | |
| 9 | 35/M | Cutaneous ALCL | skin | — | NO | POS | NEG | — | — | — |
| 10 | 50/M | Cutaneous ALCL | skin | — | NO | POS | NEG | — | — | — |
| 11 | 73/F | PTCL-U | pleura | — | NO | POS | NEG | — | — | — |
| 12 | 79/M | ALK-neg ALCL | LN | — | NO | POS | NEG | — | — | — |

FISH, fluorescence in situ hybridization; BM, bone marrow; LN, lymph node; PTCL-U, peripheral T-cell lymphoma, unspecified; ALCL, anaplastic large-cell lymphoma; PUVA, psoralen UVA photochemotherapy; IFNα-2A, interferon alpha-2A; CHOP, cyclophosphamide + hydroxydoxorubicin + oncovin + prednisone; ICE, ifosfamide + carboplatin + etoposide; ITMTX, intrathecal methotrexate; XRT, radiotherapy
*Positive for TIA-1 by immunohistochemistry.
†FISH for BCL6 at 3q27 was normal.

Two PTCL-Us with IRF4 translocations by FISH had karyotypes with t(6; 14)(p25; q11.2) (Cases 1 and 2, Table 3). Karyotypes were not performed in the other 10 PTCLs with IRF4 translocations. Karyotypes of 35 PTCLs without IRF4 translocations by FISH and 2 PTCLs in which IRF4 FISH failed exhibited no anomalies of 6p25 (Table 4). The PTCL-Us with t(6; 14)(p25; q11.2) had similar clinicopathologic features: Both presented in older adult males with mild cytopenias and without significant lymphadenopathy or hepatosplenomegaly. In both patients, imaging showed diffuse skeletal uptake and renal mass lesions. No tumor cells were seen in the peripheral blood. Both patients had extensive bone marrow infiltration by tumor with admixed plasma cells and reticulin fibrosis (FIGS. 1 (a) and (g)). The cells were larger and more pleomorphic in Case 1 (FIGS. 1 (b) and (h)). Both tumors were positive for CD3, beta-F1, TIA1, and IRF4 (FIGS. 1 (c), (d), (e), and (i)); and were negative for CD5, CD30, CD25, FoxP3 and EBV. Case 1 was positive for granzyme B and CD4, and partially positive for CD8. In both cases, the t(6; 14)(p25; q11.2) corresponded to IRF4/TCRA fusion by D-FISH (FIGS. 1 (j) and (k)). The patient in Case 1 received chemotherapy (Table 3) but developed progressive skin lesions and probable cerebrospinal fluid involvement. Despite additional therapy, his skin lesions progressed (FIG. 1 (f)). The patient in Case 2 developed skin and soft tissue lesions during the course of evaluation. These cases were classified as PTCL-Us.

TABLE 4

Cytogenetic Findings in 39 Peripheral T-cell lymphomas with Informative Karyotypes

| Age/Sex | Diagnosis | IRF4 FISH | Karyotype |
|---|---|---|---|
| 67/M | PTCL-U with IRF4/TCRA (Case 1) | POSITIVE | 48-49, XY, +3[5], +5, der(6)t(6; 14)(p25; q11.2), add(7)(p11.2), −14, +16, +16[5], −20, −22[4], +1-2mar[cp6]/95-98, idemx2, +3-8mar[2] |

TABLE 4-continued

Cytogenetic Findings in 39 Peripheral T-cell lymphomas with Informative Karyotypes

| Age/Sex | Diagnosis | IRF4 FISH | Karyotype |
|---|---|---|---|
| 71/F | PTCL-U with IRF4/TCRA (Case 2) | POSITIVE | 49, XY, +add(3)(q27), t(6; 14)(p25; q11.2), +8, −9, +19, +21 |
| 77/F | PTCL-U | NEGATIVE | 46, XX, add(11)(q23) |
| 67/M | PTCL-U | NEGATIVE | 46, XY, del(20)(q11q13.1) |
| 67/M | PTCL-U | NEGATIVE | 46, XY, add(4)(q21) |
| 57/F | PTCL-U | NEGATIVE | 46, XX, t(10; 14)(?; q11.2) |
| 62/M | PTCL-U | NEGATIVE | 47-51, XY, +X, +Y, +9, add(9)(p13)x2, +10, add(10)(p11.2), add(14)(q32), add(16)(p11.2), add(17)(p11.1), +19, +21, +0-3mar |
| 40/F | PTCL-U | | 38-44 X, −X, −4, −5, −6, −7, −8, −10, −11, −12, −18, −20, dup(1)(q25q44), der(2)t(2; ?)(p13; ?), +der(7)t(5; 7)(q13; q36),(p13; ?), der(10)(t(10; ?)(p15; ?), der(12)t(12; ?)der(19)t(19; ?)(?q13; ?), +5-7mar |
| 84/F | PTCL-U | NEGATIVE | 50-56, XX, del(2)(p23), +3, +5, +i(7q), +9, +9, +11, +14, −17, +18, +19, +mar |
| 69/M | PTCL-U | NEGATIVE | 47, XY, t(12;22)(q13; q13), t(14; 17)(q32; q21), +mar |
| 43/M | PTCL-U | NEGATIVE | 46, XY, t(5; 14)(q33; q32) |
| 78/M | PTCL-U | NEGATIVE | 50, XY, +8, +der(3), +der(4), der(6), +der(7), der(10), der(21) |
| 28/M | PTCL-U | NEGATIVE | 46, XY |
| 58/M | PTCL-U | NEGATIVE | 44-45, X-Y, add(2)(q1?3), t(3;12)(p13; q13), −4, i(7q), i(8q), del(11)(q21q23) |
| 44/M | PTCL-U | NEGATIVE | 46, XY, add(8)(q24.1) |
| 88/F | PTCL-U | NEGATIVE | 46, XX, −20, +mar |
| 65/M | PTCL-U | NEGATIVE | 55-57, XY, +2, +4, +5, +7, +8, +10, +11, +12, −13, +14, +15, +15, +16, +mar |
| 90/F | PTCL-U | NEGATIVE | 47, XX, +19[4]/48, XX, +7, +19[1] |
| 71/M | PTCL-U | NEGATIVE | 46, XY, +3, +5, +18, t(19; 22)(q13.3; q11.2) |
| 76/M | PTCL-U | NEGATIVE | 46, XY, del(3)(p13p21) |
| 76/M | PTCL-U | NEGATIVE | 46, XY, t(3; 20)(q21; q11.2) |
| 39/M | PTCL-U | NEGATIVE | 47, XY, add(13)(p13.2), add(14)(q24), add(17)(q23), +19, add(22)(q11.2) |
| 70/M | PTCL-U | NEGATIVE | 46, XY |
| 33/M | NKTL | NEGATIVE | 45, X, −Y, dup(2)(q21 -> q33), t(3; 6)(p13; q13), der(8)t(8; ?)(p21; ?) |
| 57/M | NKTL | NEGATIVE | 38-43, X, −Y, −4, −5, add(8)(q24.3), add(12)(q24.3), der(13; 22)(q10; q10), add(15)(p12), i(17)(q10), dic(18; ?)(q23; ?), add(19)(p13.3), +mar |
| 37/M | NKTL | NEGATIVE | 45-48, XY, +X, i(7)(q10), +21[cp17] |
| 56/M | LGL | NEGATIVE | 47-48, XY, inv(1)(q13q42), +3, del(5)(q13q33), dup(5)(q11.2q13), +8, add(13)(q32), add(18)(q23), +r |
| 18/F | ALCL, ALK-positive | NEGATIVE | 46, XX, t(2; 5)(p23; q35), t(9; 19)(q22; q13.1) |
| 18/M | ALCL, ALK-positive | NEGATIVE | 46, XY* |
| 56/M | ALCL, ALK-positive | NEGATIVE | 80-94, XXY-Y, add(2)(p23)x2, +5, add(5)(q33)x2, +6, +8, −9, t(11; 11)(p15; q11)x2, −15, −16, −19, −20, −21, −22 |
| 31/F | ALCL, ALK-negative | NEGATIVE | 46, XX, add(1)(p13q23), add(2)(p11.2), del(3)(q12), der(4)t(1; 4)(q23; p16), add(5)(q31), der(7)t(2; 7)(p11.2; p11.2), add(9)(q34), add(17)(p11.2), +mar |
| 50/F | ALCL, ALK-negative | NEGATIVE | 46-48, X, −X, add(2)(q37), t(5; 14)(q11.2; q11.2), add(6)(p21.3), t(9; 18)(p22;q12.2), add(11)(q13), +22, +1-2mar |
| 65/F | AITL | NEGATIVE | 46, XX |
| 71/F | AITL | FAILED | 48, XX, +5, +14, der(2), der(17) |
| 75/M | AITL | NEGATIVE | 47, XY, add(1)(p13), +der(3)t(1; 3)(p13; p13), −16, der(19)t(1; 19)(q21; q13.3), +mar |
| 76/F | AITL | FAILED | 48, XX, +2, +11 |
| 71/M | AITL | NEGATIVE | 46, XY |
| 63/M | AITL | NEGATIVE | 46, XY |
| 46/F | AITL | NEGATIVE | 46, XX |

Figure 2:
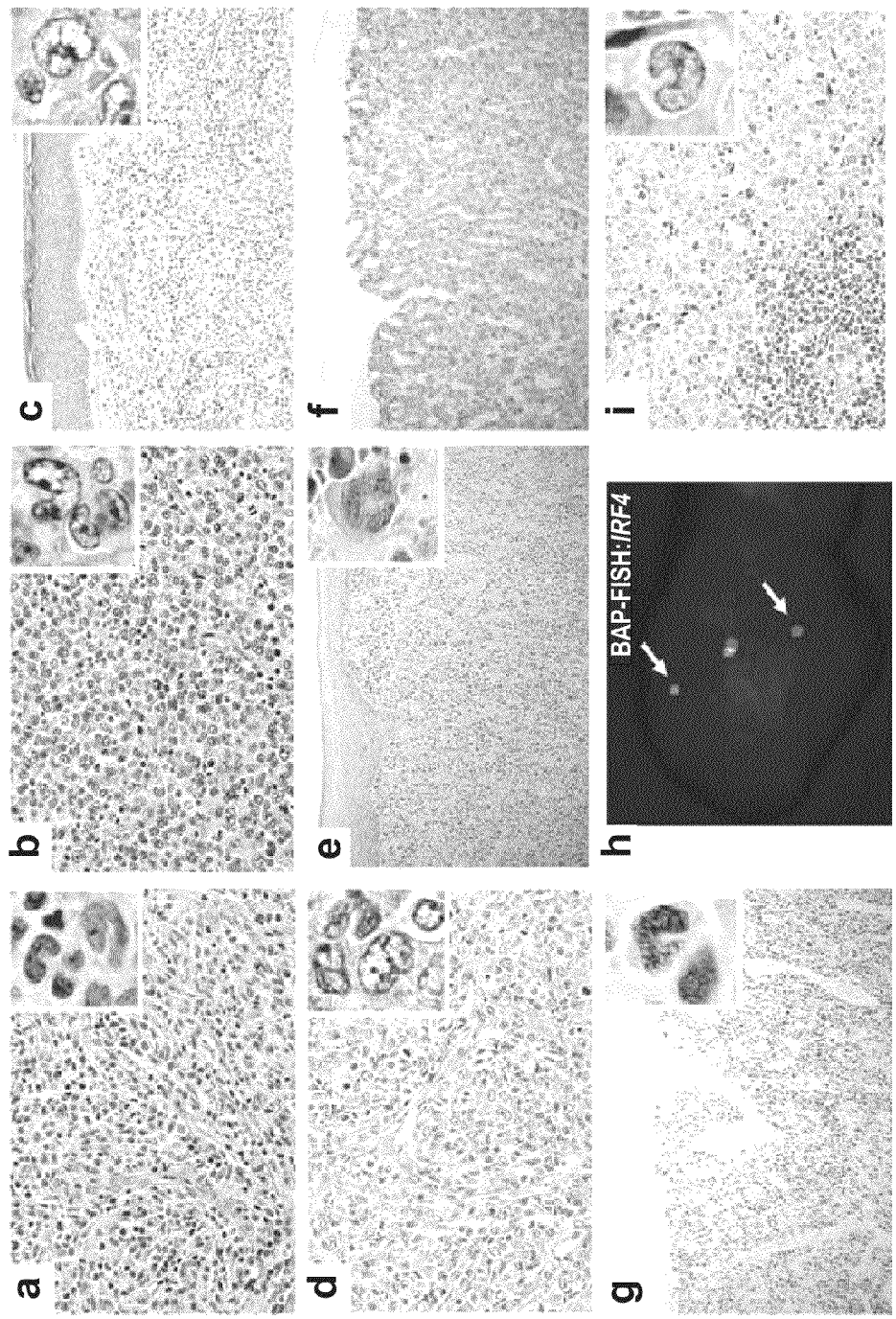
FIG. 2 shows immunohistochemistry and breakapart fluorescence in situ hybridization (BAP-FISH) identifying anaplastic large-cell lymphomas (ALCLs) with IRF4 translocations: (a) Primary cutaneous ALCL (C-ALCL), 48 year-old female (case 3) (Medium to large tumor cells with admixed histiocytes (H&E, ×40; inset, ×100)); (b) Lymph node involvement, same patient, 10 years later (Confluent sheets of large "hallmark" cells (H&E, ×40; inset, ×100)); (c) C-ALCL, 67 year-old male (case 4; H&E, ×20; inset, ×100); (d) Lymph node involvement, same patient, 7 months later (H&E, ×40; inset, ×100) (Both biopsies show sheets of "hallmark" cells); (e) C-ALCL, 89 year-old female (case 5), showing positivity for (f) CD30 and (g) IRF4 (×10; insets, ×100); (h) BAP-FISH shows separation of signals flanking the IRF4 gene locus (arrows); (i) Systemic ALK-negative ALCL, cervical lymph node, 79 year-old male (case 12) (Large "hallmark" cells surround a residual reactive follicle (lower left; H&E, ×40; inset, ×100)).

IRF4 translocations were detected in 8/14 C-ALCLs tested (57%). All initial diagnostic biopsies were reviewed. Clinical or pathologic features of lymphomatoid papulosis were not observed. None of the patients had a history of mycosis fungoides (MF) or dermatitis suggestive of clinical MF. Four patients developed nodal disease 1 to 126 months after diagnosis (Table 3). The patient with a 1-month interval between cutaneous and nodal disease (Case 7) had multiple skin nodules and local adenopathy. Staging was otherwise negative, suggesting C-ALCL with locoregional spread, however, it is possible the disease originated in the lymph node. Cases 3 and 8 showed different histology in cutaneous and nodal specimens. The skin showed mostly medium-sized tumor cells with admixed histiocytes in the background (FIG. 2 (a)), and occasional perivascular "hallmark" cells. The subsequent lymph node biopsies showed sheets of large "hallmark" cells (FIG. 2 (b)). The remaining C-ALCLs with IRF4 translocations had typical histologic features (FIG. 2 (c)-(e)). CD30 and IRF4 were positive (FIGS. 2 (f) and (g)). FISH showed IRF4 translocations (FIG. 2 (h)). C-ALCLs with and without IRF4 translocations showed similar clinicopathologic features (Table 5). TIA1 positivity was somewhat less common in IRF4-translocated cases than in untranslocated cases. Only one untranslocated case developed nodal disease.

Two additional PTCLs with translocations of IRF4 but not TCRA were identified. Case 11 was a PTCL-U in the pleura of a 73 year-old female who also had multiple lung nodules. The tumor cells were medium to large and pleomorphic. "Hallmark" cells were not seen. Staging was negative. Case 12 was an ALK-negative ALCL in a 79 year-old male with generalized lymphadenopathy but without cutaneous disease. Lymph node biopsy showed sheets of "hallmark" cells (FIG. 2(i)). Both cases were positive for CD30 and IRF4 and were non-cytotoxic. FISH for TCRB and TCRG was negative in Case 12.

TABLE 5

Clinicopathologic Features of Primary Cutaneous Anaplastic
Large Cell Lymphomas With and Without IRF4 Translocations.

|  | IRF4 Translocation | |
| --- | --- | --- |
|  | Present | Absent |
| n (%) | 8 (57) | 6 (43) |
| M:F | 6:2 | 3:3 |
| Age, mean (range), y | 60 (35-89) | 64 (12-92) |
| Immunophenotype (%) |  |  |
| CD30 | 8/8 (100) | 6/6 (100) |
| CD3 | 6/8 (75) | 2/6 (33) |
| CD4 | 5/8 (63) | 4/6 (67) |
| CD8 | 0/8 (0) | 1/6 (17) |
| ALK | 0/8 (0) | 0/6 (0) |
| TIA1 | 2/8 (25) | 3/6 (50) |
| IRF4 | 8/8 (100) | 5/6 (83) |
| Subsequent extracutaneous disease | 4 | 1 |
| Follow-up, mean (range), mos | 29 (0-154) | 30 (0-76) |

Figure 3A:
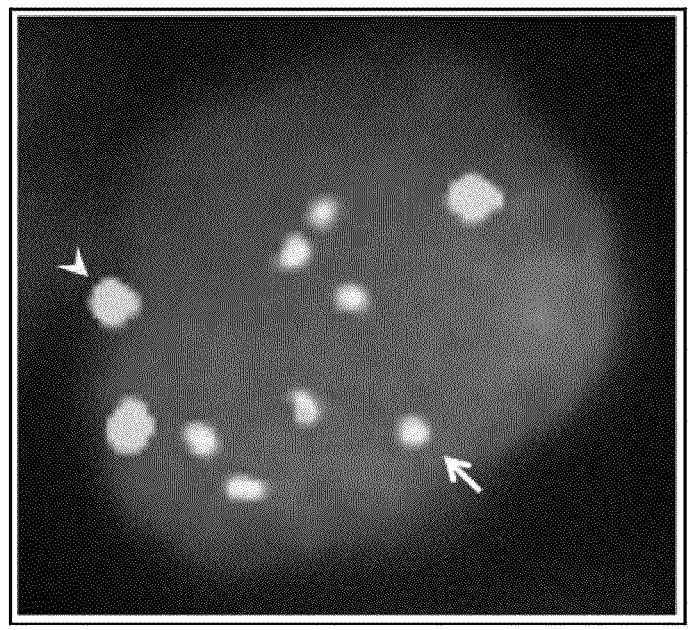
FIG. 3 shows IRF4 gene amplification and translocations in T-cell lymphomas: (A) shows BAP-FISH of a single tumor cell with 7 copies of IRF4 on 6p25 (arrow) and 3 copies of the chromosome 6 centromere (arrowhead); (B) is a bar graph showing the percentage of cases with IRF4 translocations observed in 68 skin biopsies based on cancer type (1, systemic ALK-negative ALCL; 2, systemic ALK-positive ALCL, 3, cutaneous ALCL; 4, lymphomatoid papulosis; 5, mycosis fungoides; 6, Sézary syndrome; 7, CD4-positive TCL; 8, extranodal NK/TCL; 9, subcutaneous panniculitis-like TCL; 10, peripheral TCL, unspecified).

In addition, T-cell lymphomas with amplification of the IRF4 gene locus were identified (FIG. 3A). These results demonstrate that IRF4 translocations and amplifications are associated with peripheral T-cell lymphomas.

Example 2

IRF4 Translocations Are Specific For Cutaneous Anaplastic Large Cell Lymphoma Skin biopsies involved by T-cell lymphoproliferative disorders from 68 patients were classified by WHO/EORTC criteria. Clinicopathologic data for classification included progression/regression of lesions, history of mycosis fungoides (MF) or other cutaneous T-cell lymphoproliferative disorders, anatomic site and timing of extracutaneous disease, morphology, immunophenotype, and T-cell clonality if needed. Cases that could not be classified definitively were excluded. FISH for IRF4 was performed using a breakapart probe. Positive cases also were screened for T-cell receptor (TCRA, TCRB, and TCRG) rearrangements. FISH was scored by a cytogeneticist using previously established normal ranges based on 95% confidence intervals.

Among cALCLs, 9/22 (41%) demonstrated abnormal separation of the IRF4 breakapart probe, indicating an IRF4 translocation. None of the 46 remaining T-cell lymphoproliferative disorders showed IRF4 translocations, including: 12 LyPs; six systemic ALK translocation negative ALCL; 3 systemic ALK translocation positive ALCL; 12 cases of MF (2 transformed); 2 cases of Sézary syndrome; 1 CD4+ small/medium-sized pleomorphic T-cell lymphoma; 2 extranodal NK/T-cell lymphomas, nasal type; 1 subcutaneous panniculitis-like T-cell lymphoma; and 7 peripheral T-cell lymphomas, unspecified. No rearrangements of TCRA, TCRB, or TCRG. were identified in cases with IRF4 translocations.

Figure 3B:
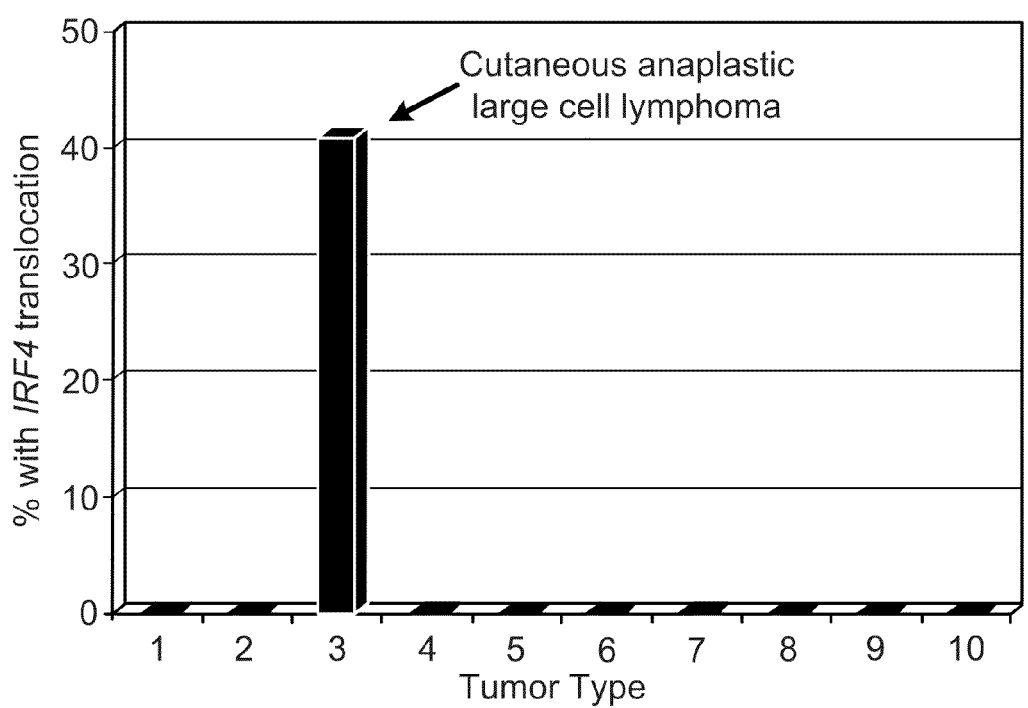
Figure 4:
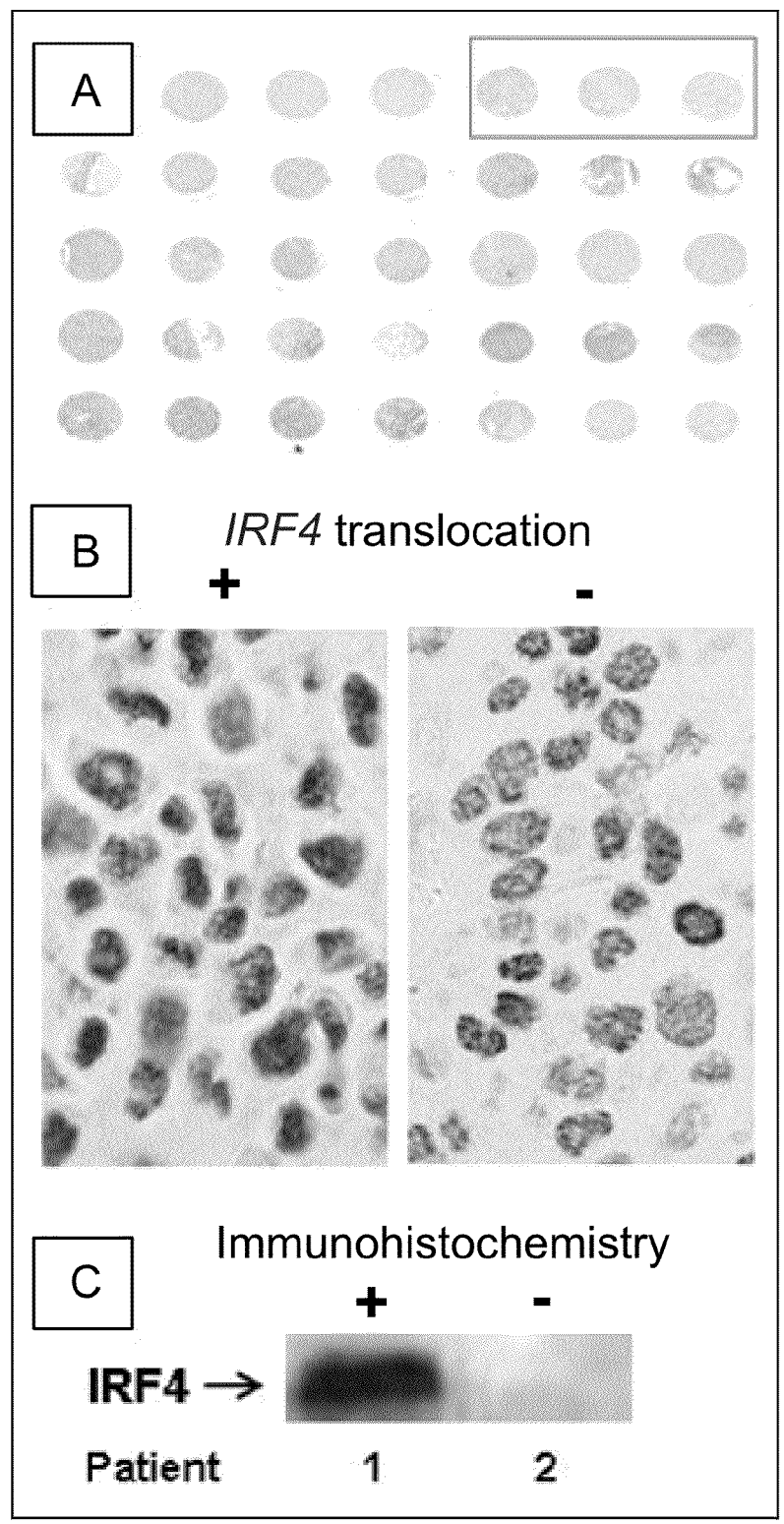
FIG. 4 (A) is a photograph of a 5 µm section of a tissue microarray stained for IRF4 by immunohistochemistry (each circle represents a section of a 0.6 mm core from a paraffin block of human T-cell lymphoma tissue, three cores are taken from each tissue block to ensure representative sampling (black box, upper right)); (B) At higher magnification, brown nuclear staining (diaminobenzidine) demonstrates IRF4 protein in the nuclei of T-cell lymphoma cells both with (left) and without (right) IRF4 gene translocations; and (C) is a western blot of IRF4 from T-cell lymphoma human tissue samples.

These results indicate that IRF4 translocations are specific for cutaneous ALCL (FIG. 3B). Furthermore, cutaneous ALCL patients with IRF4 translocations had an aggressive clinical course. For example, spread to extracutaneous sites was seen in 50% of patients with, and 17% of patients without, IRF4 translocations after similar mean follow-up intervals (FIG. 4). These findings indicate that the presence of IRF4 translocations can be a clinical biomarker for both cancer diagnosis and prognosis.

Example 3

Human T-cell Lymphoma Lines Express IRF4

Figure 5:
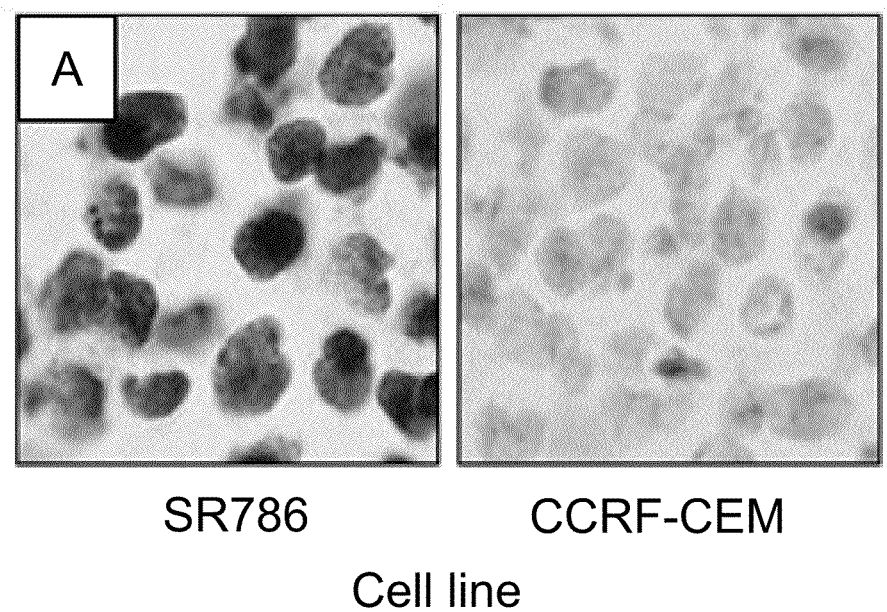
FIG. 5 (A) is a photograph of immunohistochemistry staining for IRF4 showing strong nuclear staining in SR786T-cell anaplastic large cell lymphoma cells; T-cell lymphoblastic leukemia cell lines such as CCRF-CEM were negative for IRF4 staining; (B) is a western blot for IRF4 prepared using T-cell lymphoma cell lines.
Figure 5:
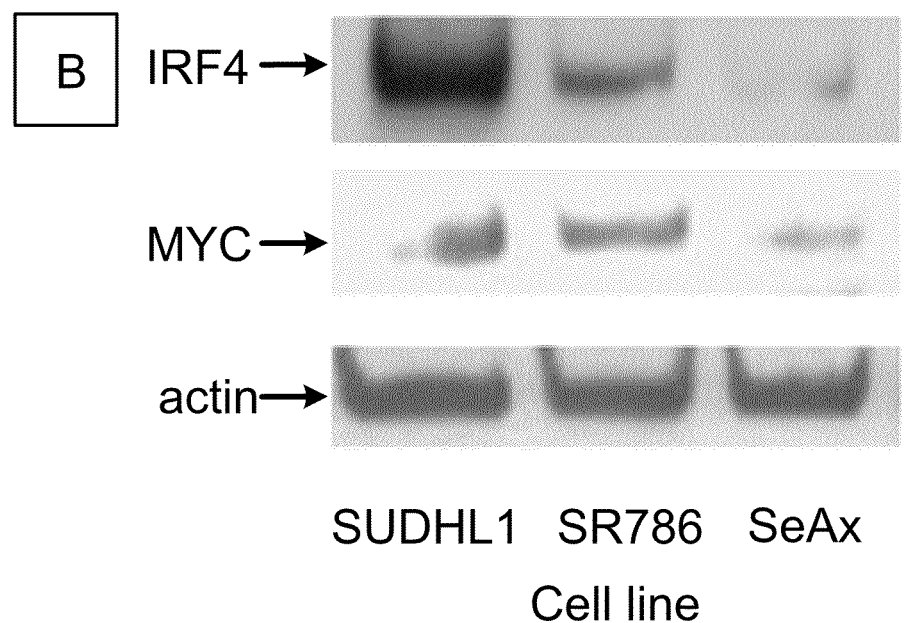

To develop an in vitro model for studying IRF4 in T-cell lymphomas, human T-cell lymphoma cell lines were screened by western blot and immunohistochemistry. All T-cell lymphomas and, T-cell lymphoma cell lines tested (SUDHL-1, SR786, Karpas 299, SeAx, MyLa, and HuT78) were positive for IRF4. T-cell lymphoblastic leukemia cell lines were negative for IRF4 (FIG. 5A). Western blotting for MYC was also performed. Cell lines with weaker IRF4 expression also showed weaker expression of MYC (FIG. 5B).

Example 4

Silencing IRF4 in T-cell Lymphoma Cells

Figure 6:
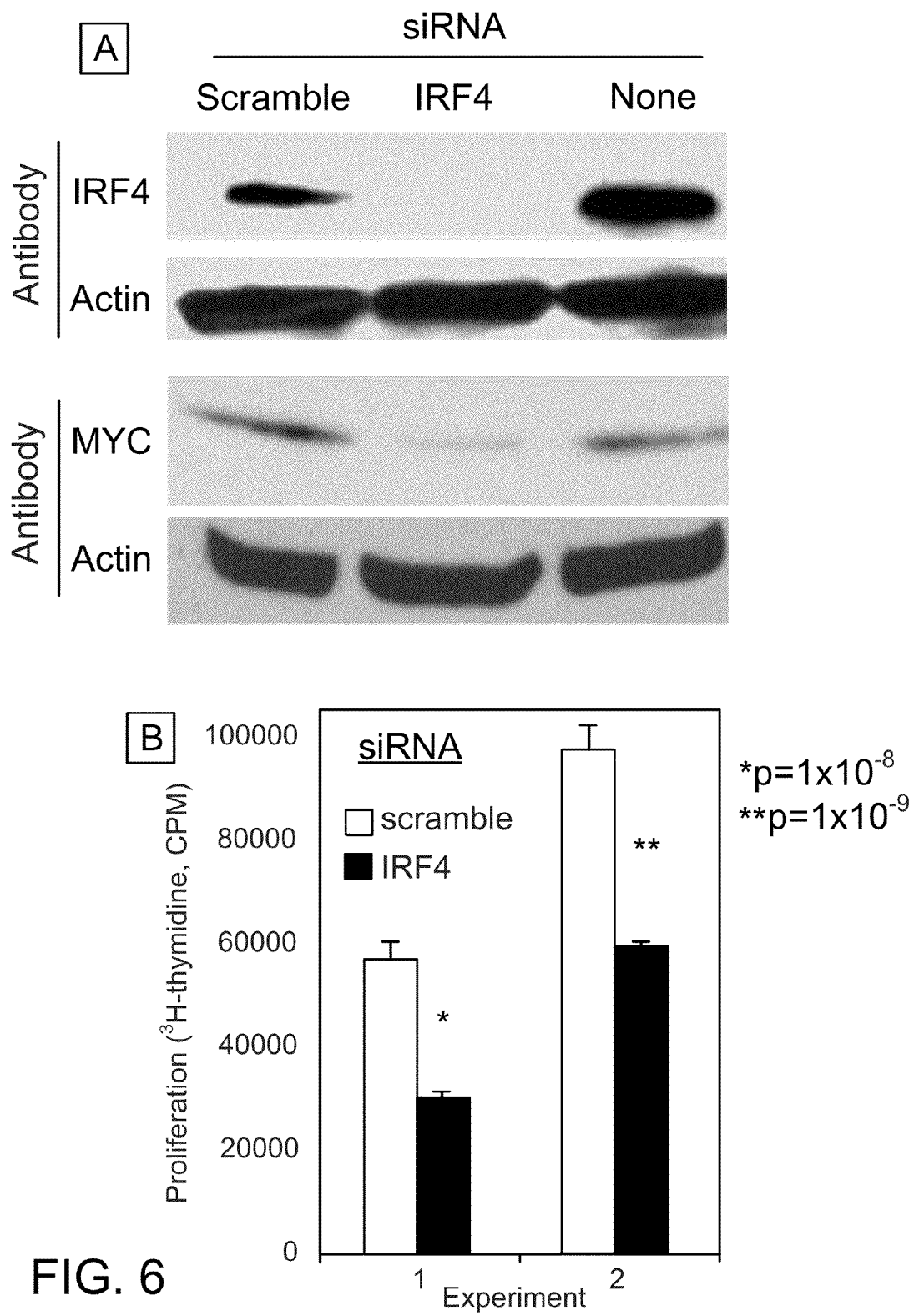
FIG. 6 (A) are western blots for IRF4, MYC, and actin prepared from SUDHL-1 T-cell lymphoma cells that were treated with either IRF4 siRNA, a control (scrambled) siRNA, or no siRNA at 48 hours; (B) is a bar graph displaying IRF4 siRNA-mediated inhibition of SUDHL-1 cell proliferation in two independent experiments by 47% and 39%, respectively ($^3$H-thymidine assay; each bar shows mean of 6 wells, error bars show S.D.).
Figure 7:
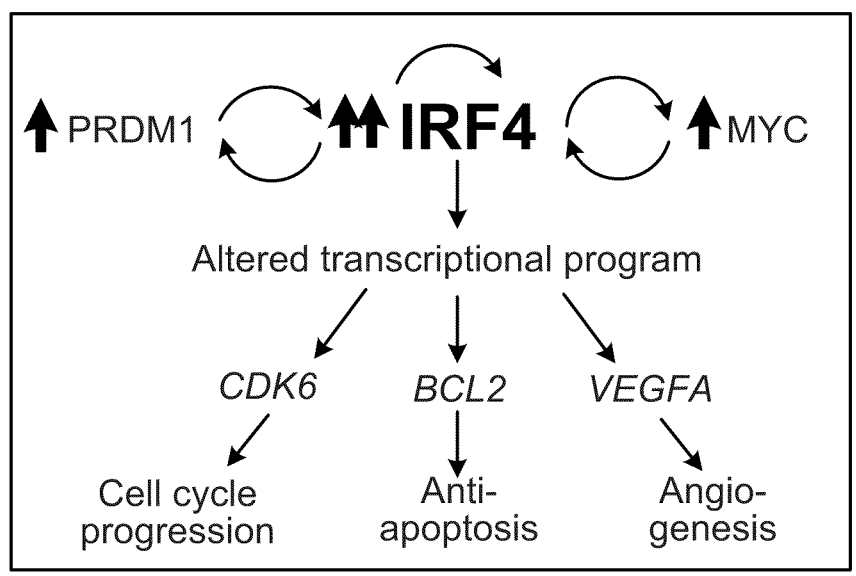
FIG. 7 is a schematic showing a proposed altered IRF4 regulatory network in T-cell lymphoma cells.

SUDHL-1 cells were transfected with either a scrambled control siRNA or IRF4 siRNA (Santa Cruz Biotechnology, Inc.). Cell lysates were assayed for protein expression by western blot. IRF4 siRNA almost completely abolished IRF4 protein expression (FIG. 6A). IRF4 siRNA, but not the control siRNA, also decreased MYC protein expression in SUDHL-1 cells. IRF4 siRNA inhibited cell proliferation by 47% and 39% in two independent experiments (FIG. 6B). These data indicate that IRF4 drives MYC expression in SUDHL-1 cells. IRF4, MYC, and PRDM1 may act together in T-cell lymphoma cells to amplify the IRF4-dependent transcriptional program, which may include genes such as CDK6, BCL2, and VEGFA (FIG. 7). Taken together, these results demonstrate that molecules designed to reduce the expression of an IRF4 polypeptide can be used to treat T-cell lymphomas.

Example 5

Use of a Massively Parallel Sequencing of Mate-Pair DNA Libraries to Detect Chromosomal Translocations in Lymphomas and Other Diseases Mate-pair library generation, massively parallel sequencing technology, and a bioinformatic algorithm were combined to detect and discover chromosomal translocations in diseased human tissue. The presence of a translocation, t(6; 7)(p25.3; q32.3), in tissue from a fatal case of systemic ALK-negative ALCL was detected. The ability to use polymerase chain reaction (PCR) and conventional sequencing to identify the precise breakpoints of translocations discovered/detected using this approach, including the t(6; 7)(p25.3; q32.3), which involve the region between exons 1 and 2 of the DUSP22 gene on chromosome 6 and the hypothetical gene region FLJ43663 on chromosome 7 was demonstrated. In addition, using a breakapart (BAP) FISH probe to the region of the breakpoint on 7q32.3, it was demonstrated that 43% of TCL cases with rearrangements at 6p25.3 have concurrent rearrangements at 7q32.3. Using a dual-fusion FISH (D-FISH) probe, it was demonstrated that 100% of such cases have FISH-based evidence of t(6; 7)(p25.3; q32.3) translocations. The presence of this translocation was specific to ALCLs lacking expression of the protein ALK. A FISH assay for the 6p25.3 gene region, which successfully distinguishes between translocations involving the IRF4 gene and those involving the DUSP22 gene, was developed. Using this approach, it was shown that t(6; 7)(p25.3; q32.3) translocations are limited to TCLs with a 6p25.3 breakpoint in the DUSP22 rather than the IRF4 gene. In addition, FLJ43663 translocations exhibited high specificity for TCLs with t(6; 7)(p25.3; q32.3) translocations, being present in <1% of TCLs without rearrangements of 6p25.3. These translocations caused up-regulation of the FLJ43663 transcript in TCLs, compared to its reported absence in normal T cells. This up-regulation existed specifically in the region of FLJ43663 that is retained on der(7),(6; 7)(p25.3; q32.3). A fusion FLJ43663/DUSP22 transcript exists derived from the t(6; 7)(p25.3; q32.3). Widely-utilized T-cell lymphoma cell lines expressed DUSP22 polypeptide, and the ability to inhibit expression of DUSP22 polypeptide in a TCL cell line using small interfering RNAs (siRNAs) was demonstrated. This inhibition of DUSP22 expression induced significant inhibition of the proliferation of the TCL cells.

A mate-pair library was prepared from genomic DNA extracted from frozen tissue (~90% tumor) from the tumor shown in FIG. 8, following the manufacturer's protocol ("Mate pair sequencing assay" from Illumina). Ten micrograms of genomic DNA in 50 µL TE buffer was added to 700 µL nebulization buffer and fragmented using nebulization for 30 seconds at 7.5 psi. This generated double-stranded DNA fragments with blunt or sticky ends with fragment sizes in the 2-5 kb range. The ends were repaired and phosphorylated using Klenow, T4 polymerase, and T4 polynucleotide kinase. Biotinylated dNTPs then were substituted for natural dNTPs at the 3' ends of the double-stranded DNA again using Klenow, T4 polymerase, and T4 polynucleotide kinase to allow for the purification of the original size selected fragments after circularization and secondary fragmentation. The resulting biotinylated constructs were separated on a 1% agarose gel. DNA fragments of approximately 5-5.5 kb were excised from the gel and purified using the Qiagen Gel Extraction Kit. Circularization of the size-selected fragments was performed by blunt end ligation for 16 hours at 16° C. using circularization ligase (Illumina). Non-circularized fragments were eliminated by DNA exonuclease treatment. The remaining circularized DNA was again fragmented, this time using the Covaris E210 (duty cycle, 5%; intensity, 3; cycles, 200; time, 180 seconds), generating double-stranded DNA fragments with fragment sizes in the 300-600 bp range. The biotinylated fragments were purified using M-280 streptavidin beads from Dynal as outlined in the Illumina mate-pair protocol. The ends of the biotinylated fragments immobilized on the beads were repaired and phosphorylated using Klenow, T4 DNA polymerase, and T4 polynucleotide kinase. An "A" base then was added to the 3' ends of double-stranded DNA using Klenow exo- (3' to 5' exo minus). Paired-end DNA adaptors (Illumina) with a single "T" base overhang at the 3' end were ligated, and the immobilized adapter-modified DNA fragments were enriched by 18 cycles of PCR using primers PE 1.0 and PE 2.0 (Illumina). The PCR supernatant was recovered from the beads using a magnetic rack. The PCR-enriched constructs were separated on a 2% agarose gel, and DNA fragments of approximately 400-600 bp were excised from the gel and purified using Qiagen MinElute Gel Extraction Kits. The concentration and size distribution of the libraries was determined on an Agilent Bioanalyzer DNA 1000 chip.

The library was loaded onto a paired-end flow cell at a concentration of 9 pM generating an average of 215,000 clusters/tile following Illumina's standard protocol using the Illumina Cluster Station and Paired-End Cluster Generation Kit, version 4. The flow cell was sequenced as a 76×2 paired-end read on an Illumina GAIIx using SBS Sequencing Kit, version 4, and SCS 2.5 Data Collection Software. Base-calling was performed using Illumina Pipeline, version 1.5.

A rough representation of a patient's entire genome was reconstructed by aligning (mapping) next generation (NG) sequencing fragments to a reference genome. Algorithms were developed to store, manipulate, and map the NG fragments and interpret the results. Mapping the 200 million NG fragments generated from an 8 lane Illumina GAIIx run can be impractical using search algorithms like BLAST; but the mapping algorithm mapped these NG fragments to a 3 billion nucleotide genome within one day.

The algorithm converted the reference genome and the NG fragments to binary numbers. This feature maximized computer memory and computational speed, and allowed the reference genome and its reverse compliment to be stored in RAM. Up to two mismatches per NG fragment were allowed to account for single point mutations and NG sequencing errors. The "good" NG fragments mapped to the reference genome exactly once and were output for analysis. Fragments that mapped multiple times were ignored. NG fragment lengths ranged from ~500 bps for a paired-end protocol, up to 5-10 kb for mate-pair protocols. For each NG fragment, only 36-100 bp of each end, called a NG tag, were sequenced by the GAIIx. The intervening sequence between the two tags was referred to as "fandom" sequence below. Accounting for the length and number of "good" fragments, the bridged coverage of the pair-end and mate-pair protocols from one lane (on the Illumina) were 0.35× and 7×, respectively. Bridged coverage referred to the entire length of each "good" NG fragment. This length included the 36-100 known sequences of each tag at both ends of the fragment and the known by distance between the two tags.

The analysis algorithms searched the mapped good NG fragments to identify genomic alterations. Putative translocations were identified when (1) each tag of a fragment mapped to two different chromosomes and (2) this pattern was observed for multiple NG fragments. The 7× bridged coverage using the mate-pair protocol was sufficient to produce the multiple observations required in step two. Deletions and amplifications as small as 10 kb were detected by: (1) counting the number of NG fragments that mapped within a specified region and (2) observing if this number exceeds or falls below an expected amount. The expected number of tags that will map within a given region was determined from a statistical method based on Extreme Value Theory. This theory was valid even for the sparse coverage achieved in pair-end protocols. Since only sparse coverage is required to detect genomic alterations, this procedure was financially preferable compared to procedures that require dense coverage.

This methodology included the following steps: (1) mapping 200 million NG fragments on a reference genome, and (2) interpretation of the mapped data to identify alterations. Multiple observations of wrong/aberrant rearrangements between chromosomes identified amplification and deletions with sparse coverage.

Mapping NG Sequencing Data to the Human Genome

The NG sequencing data were mapped to a reference genome using an algorithm. Details regarding the algorithm are set forth elsewhere (Vasmatzis et al., *Bioinformatics*, 23:1348-1355 (2007)). Briefly, the algorithm's design incorporated four main steps. The first step was to convert the reference genome and NG data to a binary representation. Each nucleotide was uniquely identified by two binary digits, for example:

| nucleotide | G | A | C | T |
|---|---|---|---|---|
| 1st binary bit | 1 | 1 | 0 | 0 |
| 2nd binary bit | 1 | 0 | 1 | 0 |

Memory storage was maximized by converting 32 consecutive nucleotides (SEQ ID NO:5) in the genome into two 32-bit binary numbers. The two numbers were referred to as the base and check arrays.

| 32 nucleotide string | GAGCCCCAAA TGCCTTCTTT GGTTTTCTTA GA |
|---|---|
| 1st 32-bit binary number: base array | 1110000111 0100000000 1100000001 01 |
| 2nd 32-bit binary number: check array | 1011111000 0111001000 1100001000 10 |

With the binary conversion, a 3.2 billion nucleotide genome was converted to ~100 million, non-overlapping 32-bit numbers. At 8 bytes per 32 nucleotides, the memory requirement for the entire genome was 800 megabytes (MB); including the reverse compliment, 1.6 gigabytes (GB).

The second step applied a forward chaining system to store large segments of the genome in RAM. The following steps 2-4 were repeated for each additional genome segment until the entire genome was analyzed. Two tables were created: (1) an Index table and (2) a Look-up table. The Index table contained two columns, the left column was the sequence of 27-bit binary numbers from 0-$2^{27}$ (111111111111111111111111111). The right column recorded the first position in the genome where the number in the corresponding left column is found. A partial Index table is illustrated below. A sequential Look-up table records all successive positions in the genome, for each 27-bit binary number, as well as all possible 32-bit base and check overlapping numbers. The length of the Look-up table was the length of the genome segment (number of positions) being stored into RAM.

Segment of the Genome, represented as 2 consecutive 32-bit binary numbers

↓ Position 1104701                    ↓ Position 1104733
... |111000011101000110000000101|01001|111000011101000110000000110| ...
    ← 27 bits →                       ← 27 bits →

Index table

| All possible 27-bit numbers Position | Genome |
|---|---|
| 000000000000000000000000000 | 0 |
| 000000000000000000000000001 | 0 |
| 000000000000000000000000010 | 0 |
| 000000000000000000000000011 | 0 |
| . | |
| . | |
| . | |
| 111000011101000110000000101 | 1104701 |
| 111000011101000110000000110 | 1104733 |
| . | |
| . | |
| 111111111111111111111111111 | 0 |

Mapping the NGS to the genome occurred in the third step by searching the Index and Look-up tables. More specifically, the left 27 bits of the NGS base array created in step 1 was found in the left column of the Index table, and the corresponding right column revealed the first genome position for that NGS. Mapping the (27-bit) NGS continued with the Look-up table to locate additional matching positions in the genome segment.

The final step used binary operation functions to compare both the base and check arrays of the entire NG tag to the genome base and check arrays. The comparison was performed using an exclusive OR operation. The output revealed the number of mismatches between the NGS and the genome. If the number of mismatches was less than a designated threshold, that position on the genome was considered a match for the NG tag, also referred to as a mapped read for the NG tag. The threshold was designated to identify a perfect match between the genome and NG tag or to allow them to differ by one or more nucleotides, thus accounting for possible mutations or sequencing errors. While some NG tags had 0 mapped reads, or over 100, only a NG tag with exactly one mapped read was written to an output file for further analysis.

This algorithm was fully automated and adaptable to rapidly map any number of NG tags to the genome. For example, over 200 million NG tags were map to a 3 billion nucleotide genome within one day using the Mayo Clinic Computer Cluster. The algorithm can be optimized to use one or both tags of a paired end or mate pair fragment.

Mapping of the Mate-Pair Lane

Figure 9:
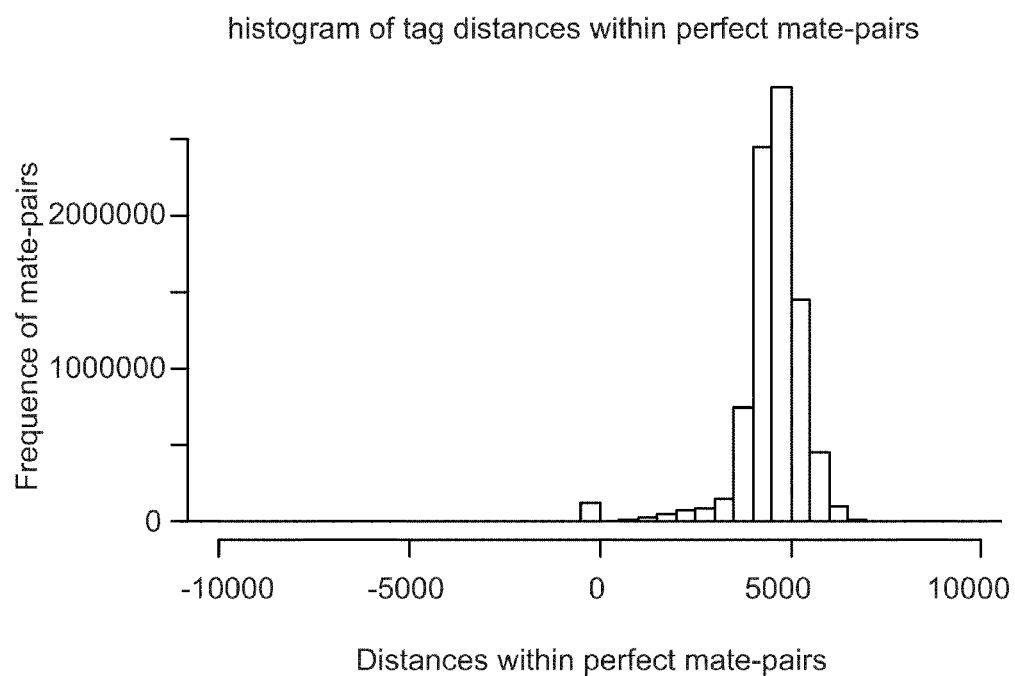
FIG. 9 is a histogram of tag distances within perfect match pairs.

One lane on the Illumina GAIIx was run by mate-pair protocol as described above. Of 28.90 million paired sequences, 21.78 million had at least one perfect (single tag)

hit across the genome. Of those, 4.19 million were considered duplicates (29%) and were eliminated. Of the 8.61 million fragments where both tags hit perfectly within chromosomes, 8.46 million were within 0 and 10 Kb with the peak at 5 kb (FIG. 9).

Coverage across the genome was as follows:

| Chromosome | max position | effective length | Bridged coverage |
|---|---|---|---|
| 1 | 249.24 | 225.09 | 15.72 |
| 2 | 243.19 | 238.23 | 15.98 |
| 3 | 197.95 | 194.81 | 16.31 |
| 4 | 191.04 | 187.72 | 15.9 |
| 5 | 180.9 | 177.31 | 15.98 |
| 6 | 171.05 | 167.46 | 16.22 |
| 7 | 159.13 | 155.31 | 15.11 |
| 8 | 146.3 | 142.82 | 16.13 |
| 9 | 141.15 | 119.44 | 14.46 |
| 10 | 135.52 | 131.24 | 15.61 |
| 11 | 134.95 | 131.19 | 15.65 |
| 12 | 133.84 | 130.54 | 15.83 |
| 13 | 115.11 | 95.62 | 16.24 |
| 14 | 107.29 | 88.3 | 15.57 |
| 15 | 102.52 | 81.6 | 15.15 |
| 16 | 90.29 | 78.86 | 14.29 |
| 17 | 81.2 | 77.83 | 14 |
| 18 | 78.02 | 74.71 | 16.37 |
| 19 | 59.12 | 55.83 | 12.05 |
| 20 | 62.97 | 59.57 | 15.76 |
| 21 | 48.12 | 35.2 | 15.45 |
| 22 | 51.24 | 34.91 | 13.2 |
| X | 155.16 | 149.61 | 7.45 |
| Y | 59.36 | 24.78 | 4.05 |

Detection of DNA Alterations, Specifically Translocations by NGS

Fragments spanning putative translocation points could be identified when each tag of a fragment maps perfectly to two different chromosomes. The actual sequence might not include these points but it is assumed that the translocation point will be within the fandom sequence of the fragment. After the ends of a fragment were identified, long range sequencing was used specifically on this fragment by amplifying it from the library. Alternatively, PCR primers were designed to PCR amplify a fragment from the original DNA pool to validate the translocation.

However, in the library preparation steps, two or more fragments from different parts of the genome were often ligated resulting in hybrid fragments that, when sequenced from both ends, look like a translocation. Since such ligations were random, it is very unlikely to find them repeatedly joining fragments from the same regions of the genome. However, real translocation will show up about as much as the bridged coverage. The 7× bridged coverage using the mate-pair protocol was sufficient to produce the multiple observations. With almost 7× bridged coverage, it was expected that real translocations would be observed multiple times. An algorithm was written to analyze the mapped data and find repeated evidence of chromosomal rearrangements.

Figure 10:
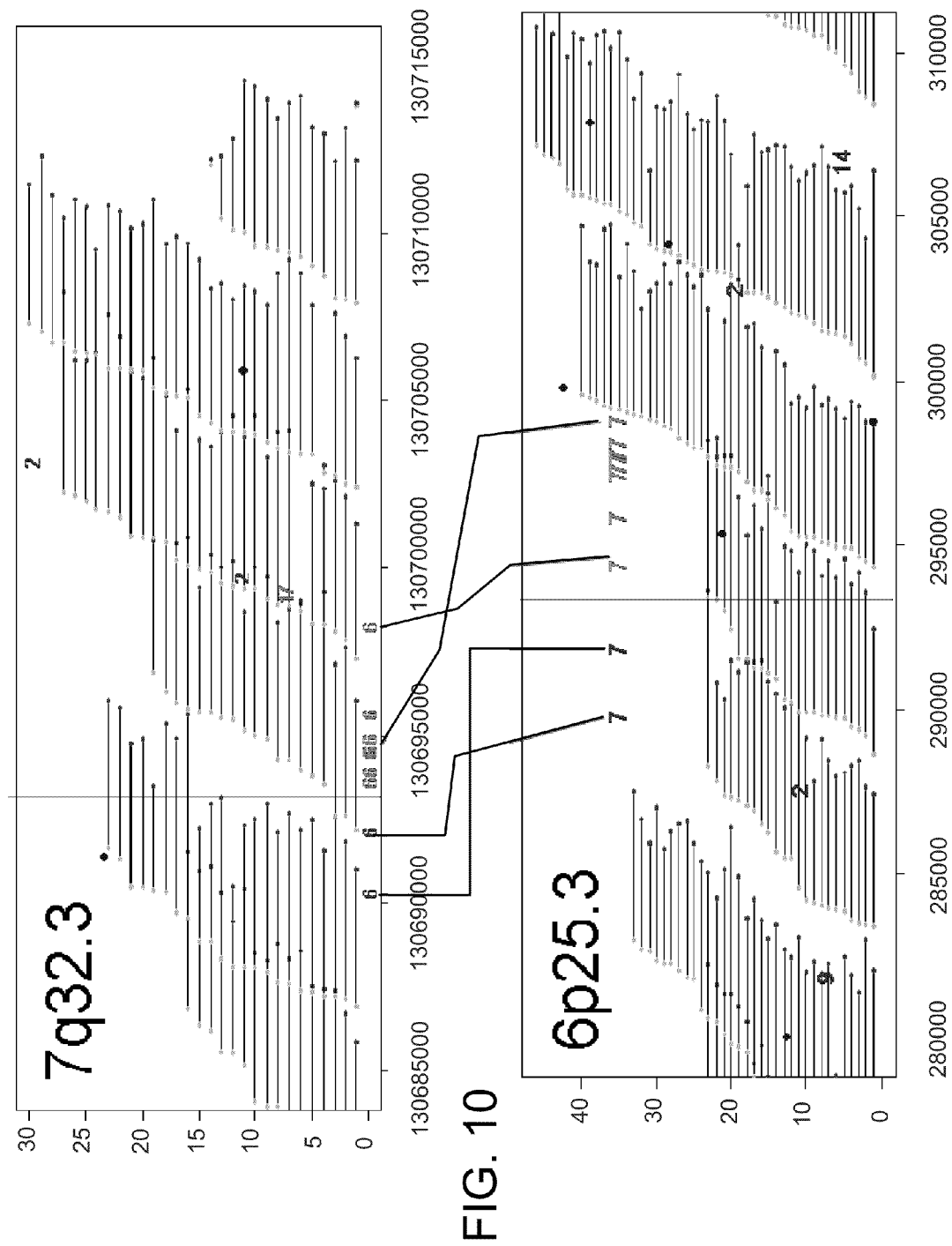
FIG. 10. Summary of results of bioinformatic analysis of mate-pair library sequencing data from the case shown in FIG. 8. The region of the known 6p25.3 rearrangement is shown in the bottom panel. The X-axis shows nucleotides according to the February 2009 genome assembly (GRCh37/hg19). Horizontal black bars represent ~5000 bp DNA fragments from which the two ends (the "mate pairs") were sequenced. The numerals in the bottom panel represent mate pairs in which one end maps to 6p25.3 and the other end maps to a different chromosome. Ten distinct (i.e. non-identical) mate pairs are seen which map to a narrow region of chromosome 7 (eight on the positive strand and two on the negative strand). In the upper panel a similar map shows the corresponding locus on 7q32.3, with the numerals showing the sites of the same 10 aberrant mate pairs. Since these aberrant mate pairs have ends that map to distinct regions of the genome, they suggest a possible translocation between loci adjacent to these paired ends. Occasional single numerals (e.g. the numeral "14" in the lower right of the bottom panel) represent sporadic, non-repeated, aberrant mate pairs that may be introduced during the ligation step of the mate-pair library preparation. Thus, the number of non-identical mate-pairs with ends mapping to distinct genomic regions (e.g. 6p25.3 and 7q32.3 in the above diagram) is a criterion in identifying putative translocations. The putative breakpoints will lie between the positive-strand mate pairs and the negative-strand mate pairs. In this case, subsequent PCR and sequencing (see below) confirmed the breakpoints at the regions indicated by the vertical lines.
Figure 11:
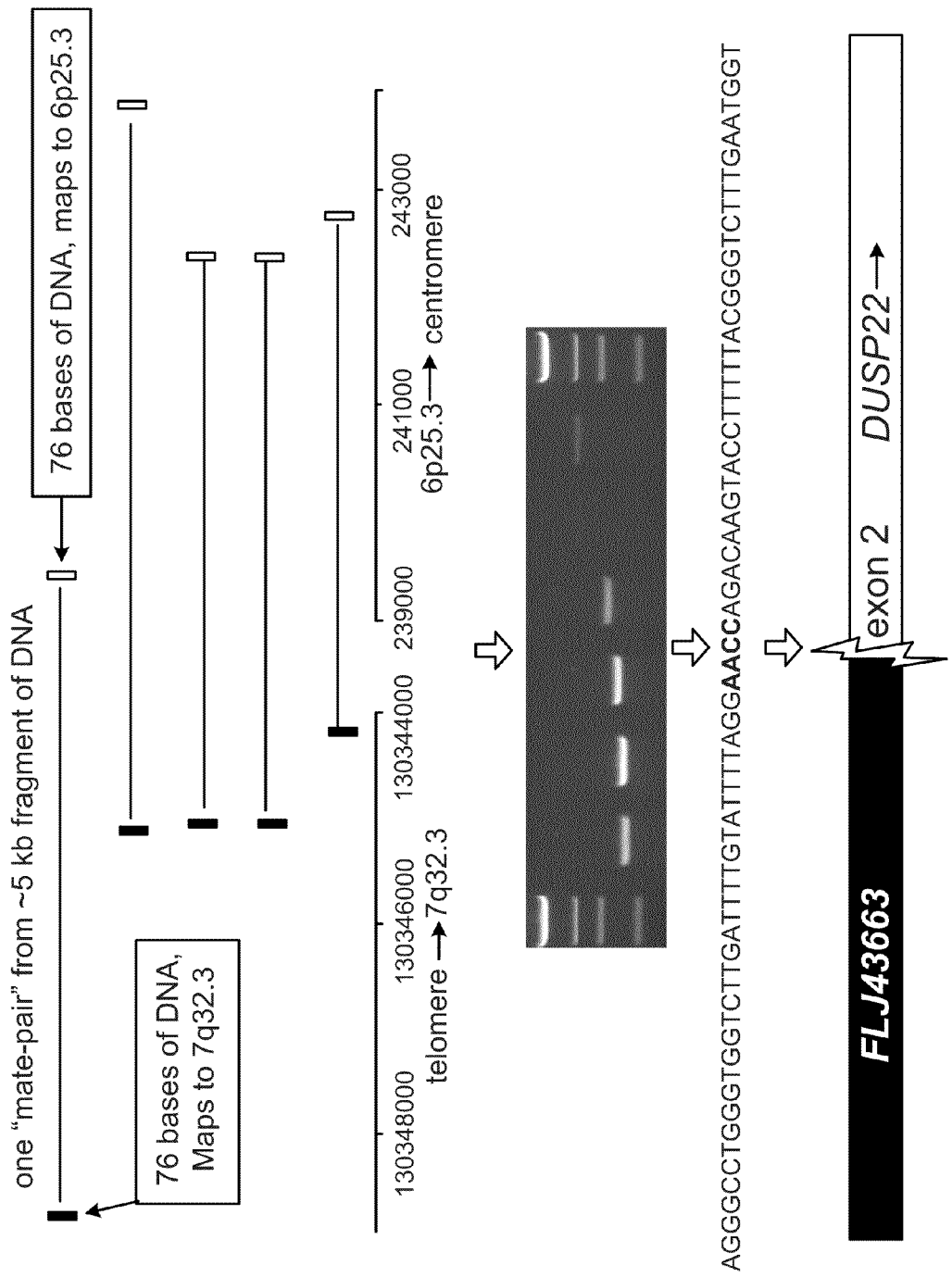
FIG. 11. Sequence mapping of the der(6)t(6; 7)(p25.3; q32.3). Five representative mate pairs are shown in the top panel. For each mate pair, one end maps to 6p25.3 (black boxes) and the other end maps to 7q32.3 (shaded boxes). Primers designed to amplify the intervening DNA (which includes the breakpoint) were used to produce the PCR bands shown in the gel image. These bands were excised and DNA was extracted and sequenced (SEQ ID NO:6). Sequences were mapped to the genome using the BLAT tool available at "http," colon, slash, slash, "genome.ucsc.edu," slash, "cgi-bin/hgBlat?command=start&org=Human&db=hg19&hgsid=159409307." This analysis indicated the translocation joins the FLJ43663 hypothetical gene region on 7q32.3 with the DUSP22 gene on 6p25.3.

Bioinformatic analysis of the mate-pair library sequencing data indicated a putative t(6; 7) translocation, with 10 aberrant mate pairs, each showing one end mapping to 6p25.3 and the other to 7q32.3 (FIG. 10). To confirm this translocation, PCR primers were designed spanning the putative breakpoints on the derivative chromosomes 6 and 7. These confirmed the presence of two hybrid segments of genomic DNA, each composed partly of material from the DUSP22 locus on 6p25.3 (with a breakpoint with the intron between exons 1 and 2), and partly of material from the FLJ43663 hypothetical gene locus on 7q32.3. The results from analysis of the der(6) are shown in FIG. 11.

Figure 12B:
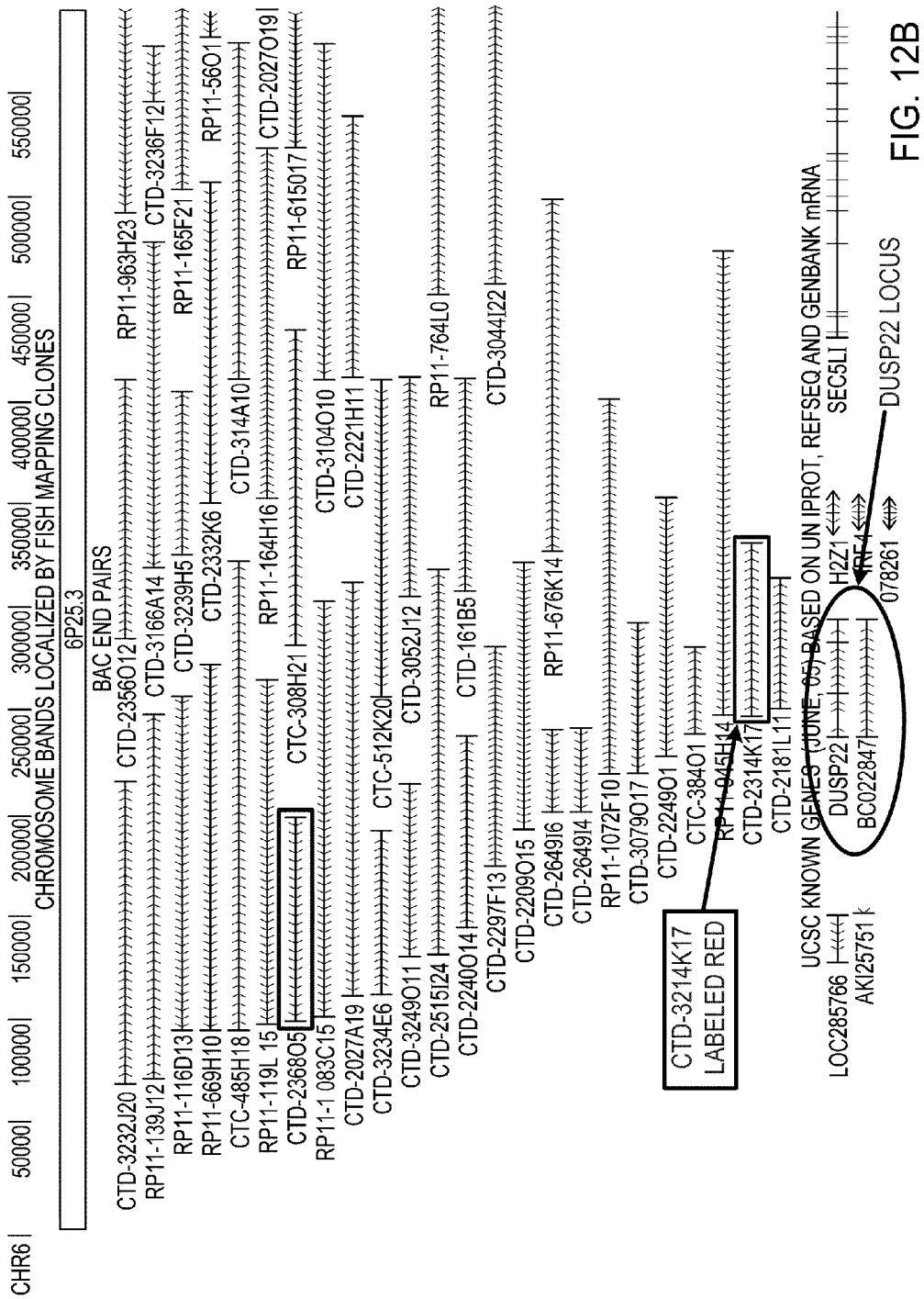
FIG. 12. Breakapart FISH probes designed to differentiate IRF4 translocations (Probe #3)(A) from DUSP22 translocations (Probe #4)(B) in cases with known rearrangements of the 6p25.3 region (as determined by abnormal signal separation using Probe #2). The red-labeled probe (CTD-2314K17) cross-hybridizes to 16p11 (not shown), and these resultant extra red signals must be taken into account when interpreting the results of FISH using Probes #3 and #4 (see FIG. 6, below).
Figure 13:
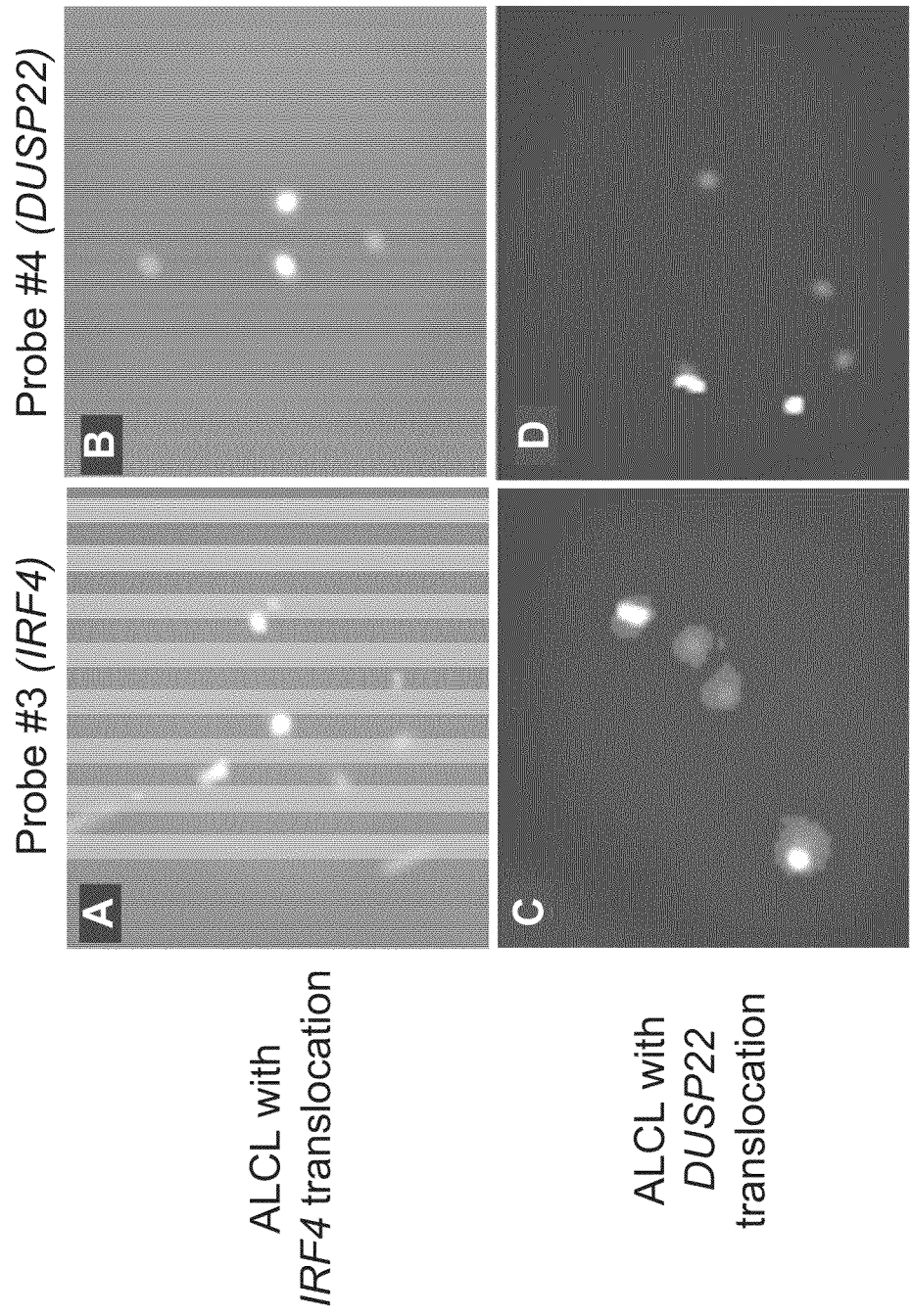
FIG. 13. Use of breakapart FISH Probes #3 and #4 to differentiate IRF4 translocations from DUSP22 translocations in cases with known 6p25.3 rearrangements. Above, a case of ALCL shows abnormal separation of green and red signals using Probe #3, with two additional red signals attributable to cross-hybridization (A). The same case shows a normal signal pattern with Probe #4 (two fusion signals and two red cross-hybridization signals) (B); thus, this case has an IRF4 translocation. Below, a case of ALCL shows a normal signal pattern with Probe #3 (two fusion signals and two red cross-hybridization signals) (C), but shows abnormal separation of green and red signals using Probe #4, with two additional red signals attributable to cross-hybridization (D); thus, this case has a DUSP22 translocation.
Figure 14:
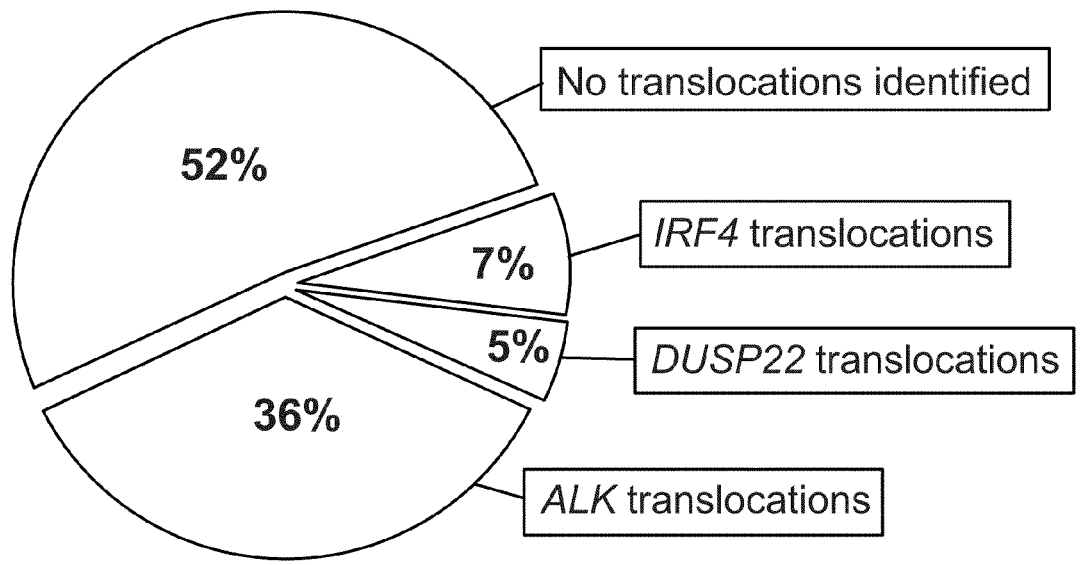
FIG. 14. Results of a FISH study of 82 Mayo Clinic patients with ALCL, performed by screening cases for 6p25.3 rearrangements with Probe #2 (FIG. 1B), and testing cases with abnormal signal separation using Probes #3 and #4 to distinguish between IRF4 and DUSP22 translocations (FIGS. 5 and 6). ALK immunohistochemistry was used as a surrogate for the presence of ALK translocations. Notably, IRF4 and DUSP22 translocations occurred only in ALK-negative cases.

The finding of a translocation involving DUSP22 led to the development of BAP FISH probes that could examine cases with 6p25.3 rearrangements and differentiate translocations involving DUSP22 from those involving IRF4 (FIG. 12). Representative FISH images showing the use of these probes are shown in FIG. 13. The screening probe, Probe #2 (FIG. 8B), was used to confirm the presence of a 6p25.3 rearrangement, since without this step the extra signals attributable to cross-hybridization cannot be accurately interpreted. In an analysis of 82 patients with ALCL, DUSP22 translocations were seen in 5%, IRF4 translocations were seen in 7%, and ALK expression (a surrogate for the presence of ALK translocations (Jaffe, Mod. Pathol., 14:219-228 (2001)) was seen in 36% (FIG. 14). All cases with DUSP22 or IRF4 translocations were ALK negative.

Figure 8A:
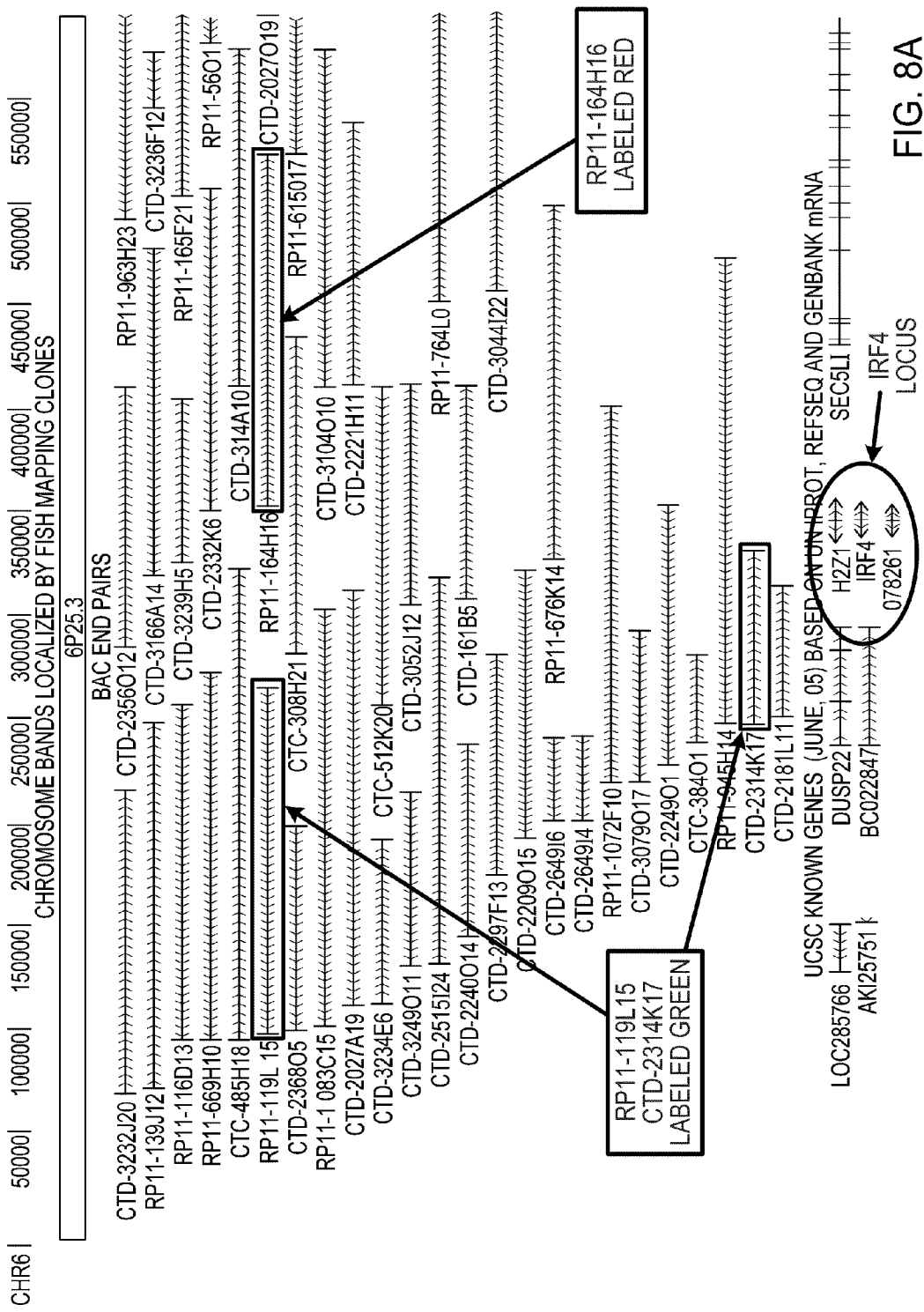
FIG. 8. Fluorescence in situ hybridization (FISH) in a fatal case of ALK-negative anaplastic large cell lymphoma (ALCL). Breakapart FISH probes to the 6p25.3 region included Probe #1 and Probe #2 as published. 16 Probe #1 is specific for the IRF4 locus (A), while Probe #2 is less specific and also encompasses the DUSP22 locus (B). Panel (C) shows morphology typical of ALCL; immunohistochemical stains showed positivity for CD30 and negativity for ALK (not shown). No IRF4 translocation was detected by FISH using Probe #1 (not shown). Panel (D) shows the result of FISH using Probe #2. The separated red and green signals (arrows) indicate a translocation. Since this pattern was not seen with Probe #1, a DUSP22 translocation is suggested.
Figure 8B:
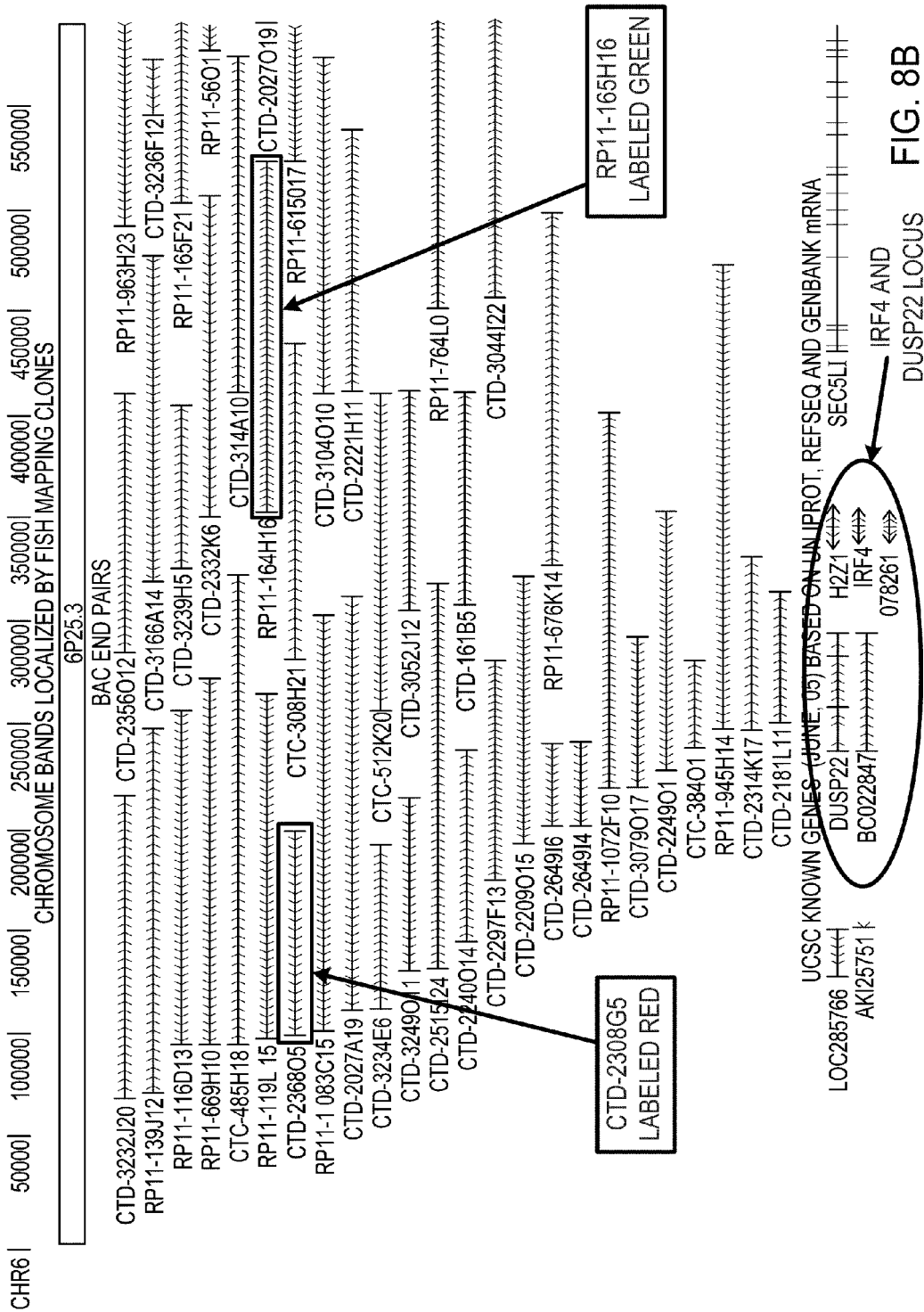
Figure 8C:
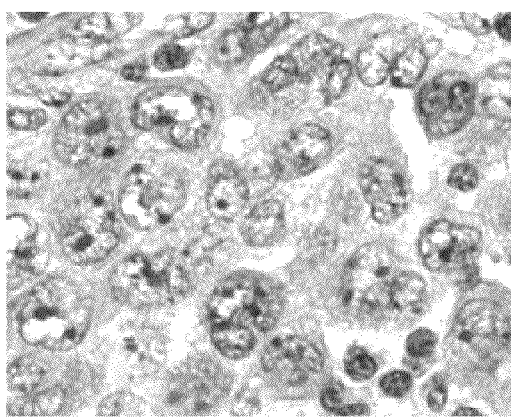
Figure 8D:
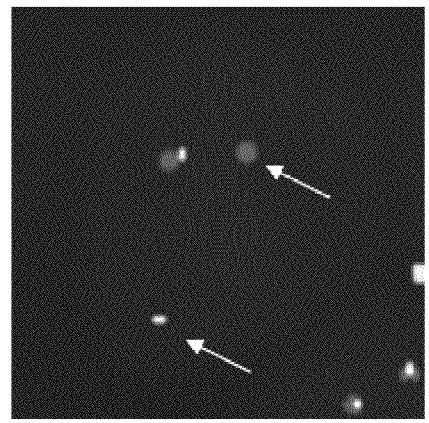
Figure 15:
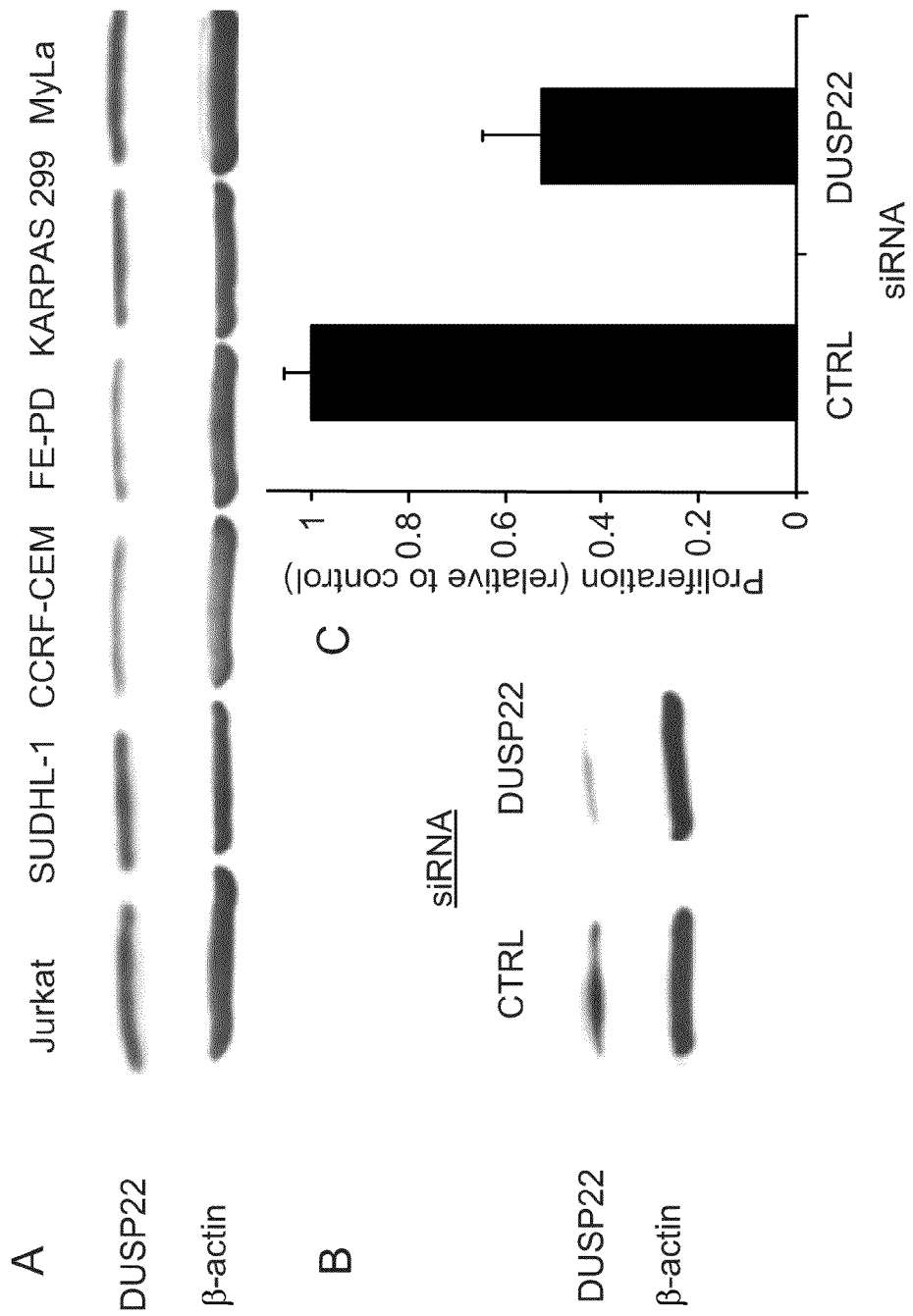
FIG. 15. DUSP22 expression and activity in TCLs. (A) Western blotting shows DUSP22 expression in all TCL cell lines tested, including T-lymphoblastic leukemias/lymphomas (Jurkat and CCRF-CEM), mycosis fungoides/Sezary syndrome (MyLa), ALK-positive ALCLs (SUDHL-1 and Karpas 299), and ALK-negative ALCL (FE-PD). (B) DUSP22 protein is down-regulated in SUDHL-1 ALCL cells after treatment with a DUSP22-specific small interfering RNA (siRNA). (C) SUDHL-1 cells treated with DUSP22-specific siRNA show a 43% reduction in proliferation compared to those treated with control siRNA.

DUSP22 is a dual-specificity phosphatase whose major role is in modulating mitogen-activated protein kinase (MAPK) signaling (Patterson et al., Biochem. J., 418:475-489 (2009)). DUSP22 expression was analyzed in 6 TCL cell lines. DUSP22 was expressed in all lines tested (FIG. 8A). SUDHL-1, an ALCL cell line, was selected for further studies. SUDHL-1 cells were treated with small interfering RNAs (siRNAs) to determine the effect of DUSP22 silencing on cell proliferation. Cells were treated either with a pool of three siRNAs specific for DUSP22, or an irrelevant control siRNA (Santa Cruz Biotechnologies). Western blotting at 48 hours confirmed that the cells treated with DUSP22 siRNAs down-regulated expression of DUSP22 protein (FIG. 15B). Radioactivity was measured in a scintillation counter 48 hours after siRNA treatment and 16 hours after the addition of tritiated ($^3$H—) thymidine. Cells treated with DUSP22 siRNA exhibited a 43% decrease in proliferation compared to cells treated with control siRNA (FIG. 15C). This decrease was statistically significant (p<0.000001, Student's t test). These results suggest that the activating functions of DUSP22 TCL cells outweigh its inhibitory functions, and that DUSP22 may have oncogenic function in TCLs.

Figure 16:
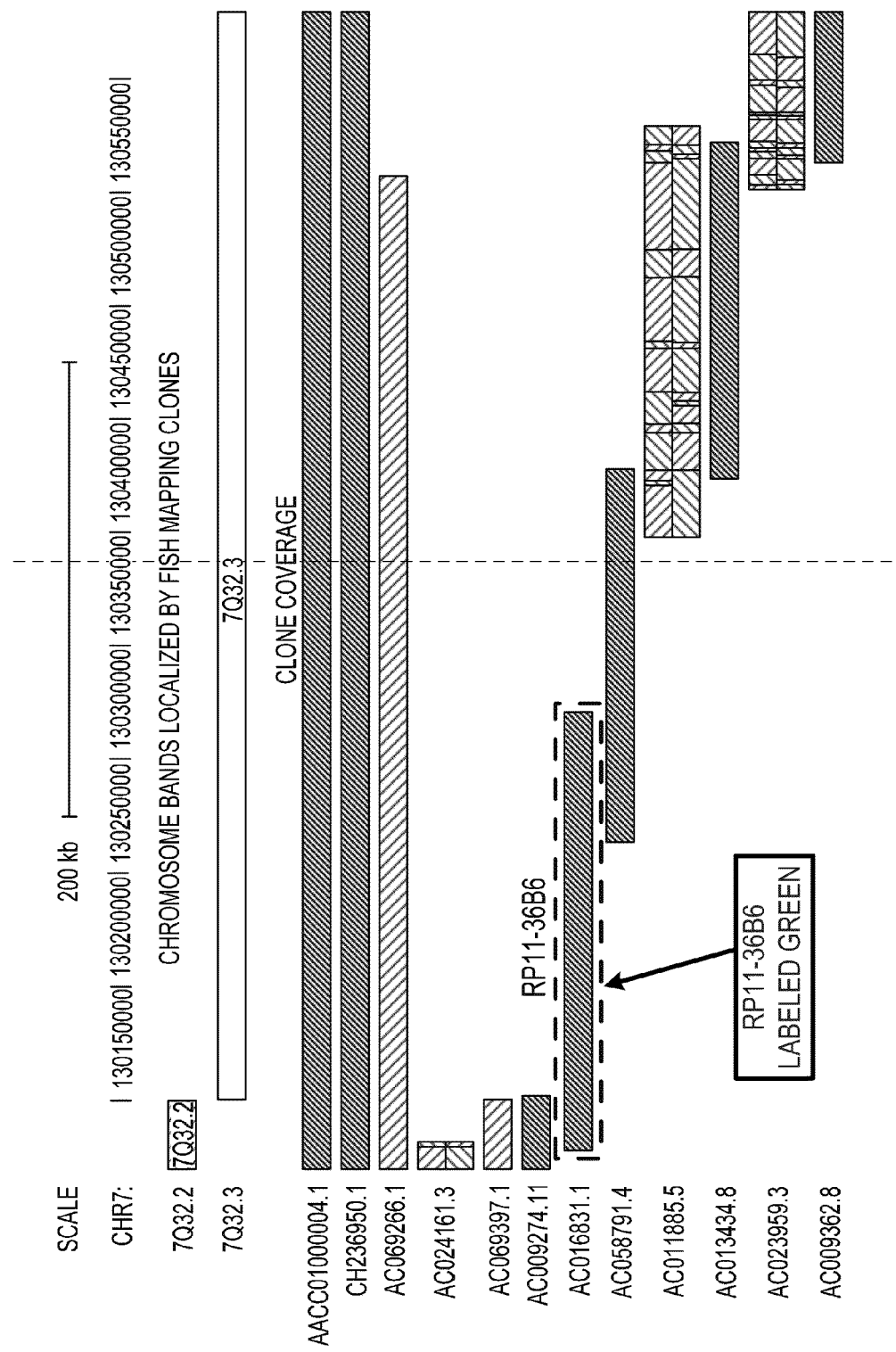
FIG. 16. Breakapart FISH probe to FLJ43663 hypothetical gene region on 7q32.3. DNA from the centromeric and telomeric bacterial artificial chromosomes (BACs) is labeled green or red, respectively, as shown. The breakpoint identified in the sequenced case (FIG. 8) is shown by the vertical dotted line.
Figure 16:
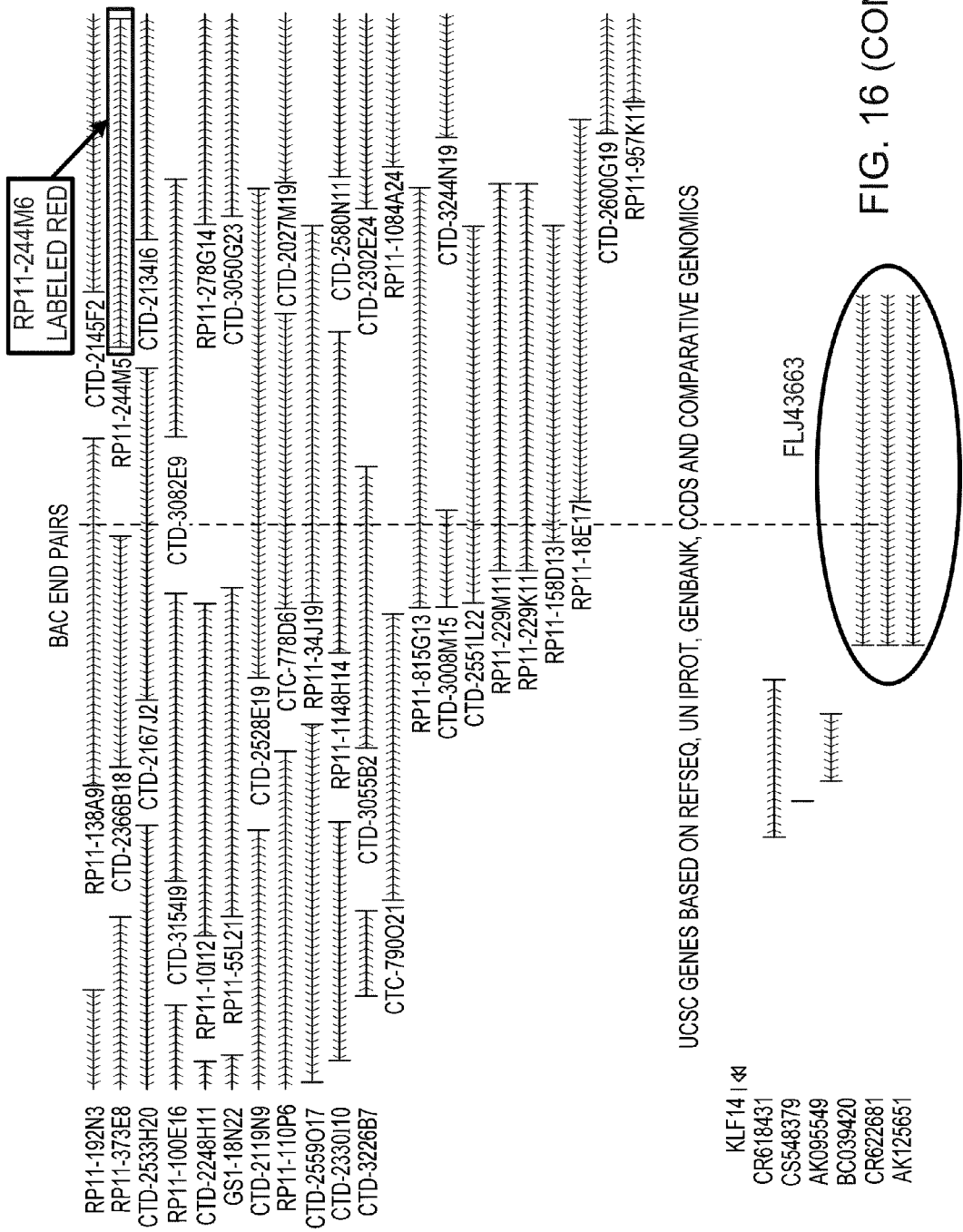
Figure 17:
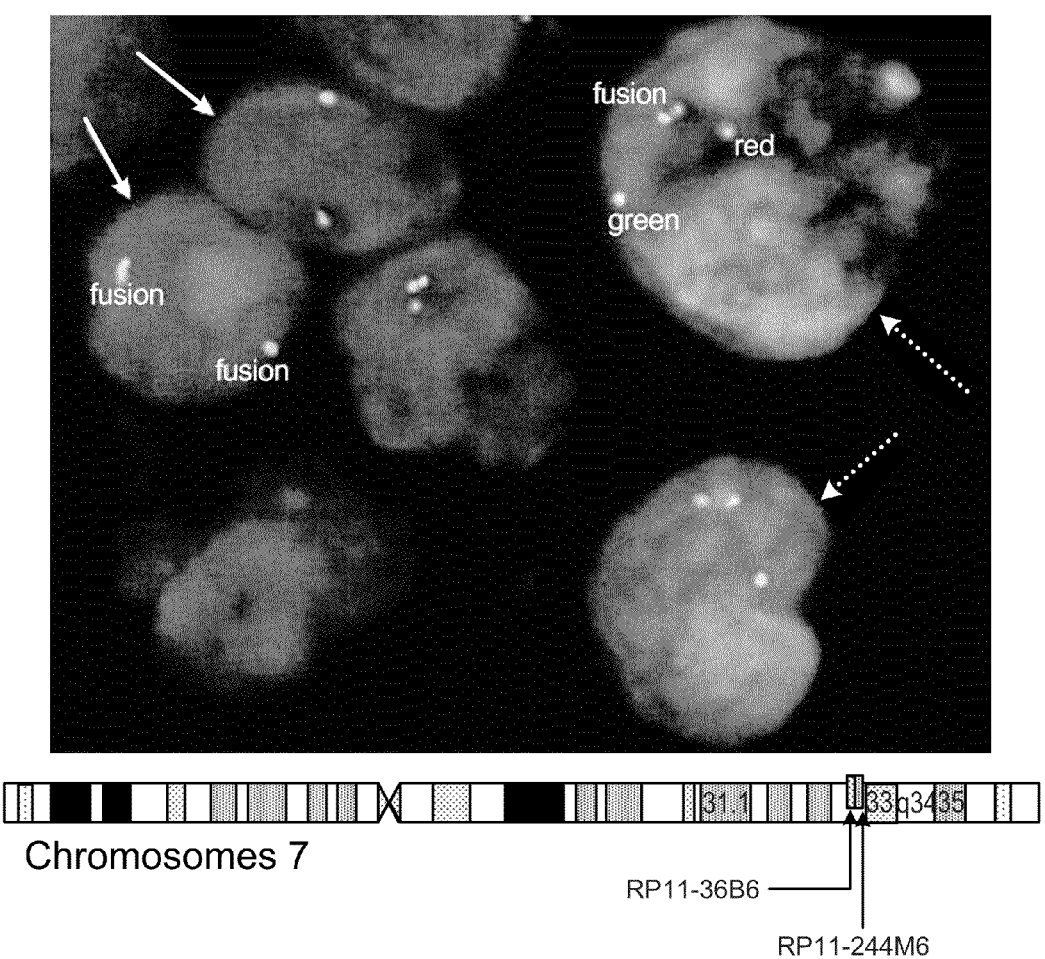
FIG. 17. FISH using the 7q32.3 BAP probe on a section from the sequenced tumor. Nuclei are stained blue (appears gray). Dotted arrows indicate cells showing abnormal separation of the red and green signals, indicating a translocation. Solid arrows indicate cells with a normal signal pattern (2 fusion signals). Below, the location of the probe on chromosome 7 is shown.
Figure 18:
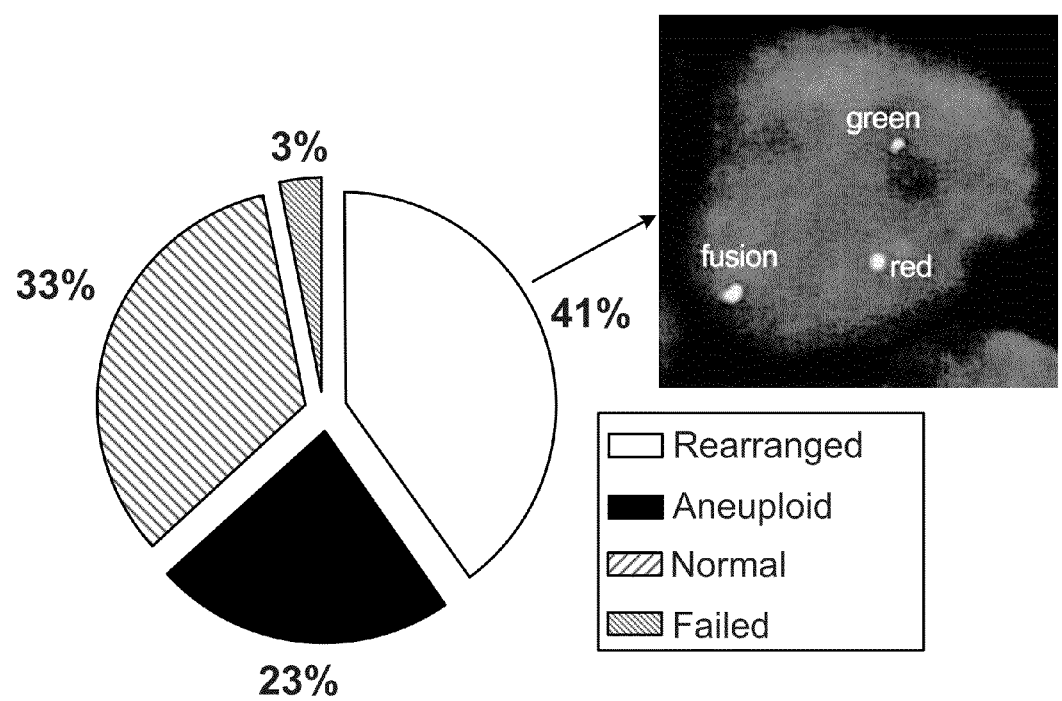
FIG. 18. Results of 7q32.3 BAP FISH in 30 TCLs with known 6p25.3 rearrangements. Concurrent rearrangements of 7q32.3 were seen in 41% of the cases (representative FISH image shown in lower right). An additional 23% had extra copies of the FLJ43663 locus (aneuploid), while one-third of cases showed a normal signal pattern.

To determine whether the t(6; 7)(p25.3; q32.3) translocation occurs in other TCLs, a BAP FISH probe to the 7q32.3 locus containing the FLJ43663 hypothetical gene region was designed (FIG. 16). The probe exhibited separation of the red and green signals in the sequenced case described above, which then served as a positive control (FIG. 17). Then, 29 additional TCL cases (30 cases overall), which were previously revealed to have 6p25.3 rearrangements (Feldman et al., Leukemia, 23:574-580 (2009) and Wada et al., Mod. Pathol., 22 suppl 1:289 A (abst 1308) (2009)), were tested using the 7q32.3 BAP FISH probe. Rearrangements of 7q32.3 were seen in 41% of these cases (FIG. 18). Interestingly, another 23% exhibited extra copies of the unrearranged FLJ43663 locus.

Figure 19:
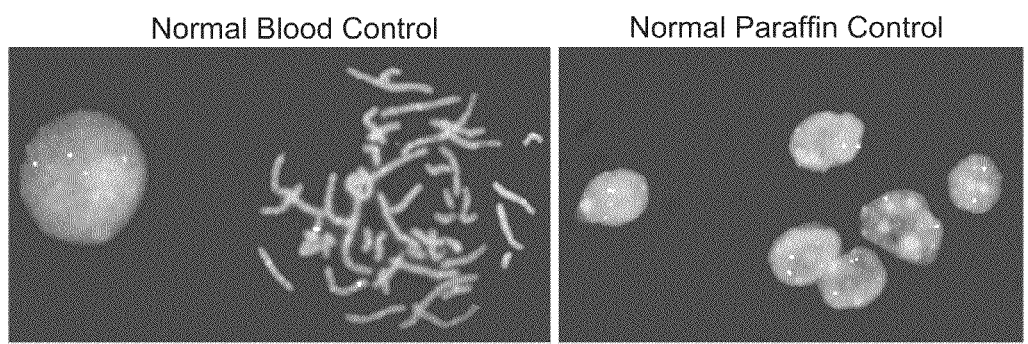
FIG. 19. Validation of the t(6; 7)(p25.3; q32.3) dual-fusion FISH (D-FISH) probe. The probe was constructed by labeling DNA from both BACs in 6p25.3 Probe #2 (FIG. 1B) red, and DNA from both BACs in the 7q32 probe. The red and green signals are seen to hybridize to their respective loci in a metaphase from peripheral blood (left), and show a normal signal pattern in a paraffin section of a lymph node (right: 2 red signals and 2 green signals in each cell).

To determine whether the cases with both 6p25.3 and 7q32.3 rearrangements had t(6; 7)(p25.3; q32.3) translocations (rather than two unrelated translocations), a dual-fusion FISH (D-FISH) probe was developed to detect the t(6; 7)(p25.3; q32.3) (FIG. 19). A summary of the FISH results is given in Table 6. Cases with 6p25.3 rearrangements were subdivided according the their 6p25.3 breakpoint based on FISH using Probes #3 and #4 as shown in FIGS. 12 and 14. Among cases with successful hybridizations, this method successfully localized the breakpoint to either IRF4 or DUSP22 in all but one case (Case 13) in which results were indeterminate. Of the 12 cases with a FLJ43663 break detected by the 7q32.3 BAP probe, D-FISH confirmed the presence of a t(6; 7)(p25.3; q32.3) in 10, and the hybridization failed in 2. Interestingly, in all cases with a confirmed t(6; 7)(p25.3; q32.3), the breakpoint on 6p25.3 lay within the DUSP22 gene region, rather than within IRF4 (though Case 10 had concurrent IRF4 and FLJ43663 breaks but D-FISH could not be interpreted). Of the 10 cases with t(6; 7)(p25.3; q32.3), 5 exhibited only 1 fusion signal, suggesting probable unbalanced translocations. In the remaining 5 cases, 2 fusion signals were seen in at least some cells, suggesting balanced translocations.

TABLE 6

Genetic characteristics of 30 cases of T-cell lymphomas with 6p25.3 rearrangements.

| Case | Age | Sex | Diagnosis | Breakpoint on 6p25.3* | 7q32.3 Breakapart FISH | t(6; 7) (p25.3; q32.3) D-FISH | Number of Fusion Signals |
|---|---|---|---|---|---|---|---|
| 1 | 79 | M | ALCL, ALK– | DUSP22 | Break | Fusion | 1-2 |
| 2 | 89 | F | cALCL | DUSP22 | Break | Fusion | 1-2 |
| 3 | 50 | M | ALCL, ALK– | DUSP22 | Break | Fusion | 1-2 |
| 4 | 68 | M | cALCL | DUSP22 | Break | Fusion | 1 |
| 5 | 65 | M | cALCL | Hyb. fail. | Break | Fusion | 1 |
| 6 | 65 | M | ALCL, ALK– | DUSP22 | Break | Fusion | 1 |
| 7 | 50 | M | cALCL | DUSP22 | Break | Fusion | 1 |
| 8 | 65 | M | ALCL, ALK– | DUSP22 | Break | Fusion | 2 |
| 9† | 46 | M | ALCL, ALK– | DUSP22 | Break | Fusion | 2 |
| 10 | 77 | M | cALCL | IRF4 | Break | Hyb. fail. | |
| 11 | 65 | M | ALCL, ALK– | Hyb. fail. | Break | Hyb. fail. | |
| 12 | 66 | F | cALCL | DUSP22 | Break** | Fusion | 1 |
| 13 | 57 | M | cALCL | Indeterminate | Aneuploid | | |
| 14*** | 76 | M | cALCL | DUSP22 | Aneuploid | | |
| 15*** | 76 | M | cALCL | Hyb. fail. | Aneuploid | | |
| 16 | 59 | F | cALCL | IRF4 | Aneuploid | | |
| 17 | 66 | M | cALCL | DUSP22 | Aneuploid | | |
| 18 | 65 | F | cALCL | Not done | Aneuploid | | |
| 19 | 52 | M | cALCL | IRF4 | Aneuploid | | |
| 20 | 71 | F | cALCL | DUSP22 | Normal | | |
| 21 | 50 | M | ALCL, ALK– | DUSP22 | Normal | | |
| 22 | 54 | M | ALCL, ALK– | DUSP22 | Normal | | |
| 23 | 33 | F | ALCL, ALK– | DUSP22 | Normal | | |
| 24 | 86 | M | cALCL | Hyb. fail. | Normal | | |
| 25 | 35 | M | cALCL | IRF4 | Normal | | |
| 26 | 54 | M | ALCL, ALK– | IRF4 | Normal | | |
| 27 | 56 | F | cALCL | IRF4 | Normal | | |
| 28 | 45 | M | cALCL | Hyb. fail. | Normal | | |
| 29 | 62 | M | ALCL, ALK– | IRF4 | Normal | | |
| 30 | 73 | F | PTCL, NOS | Hyb. fail. | Hyb. fail. | | |

Abbreviations: FISH, fluorescence in situ hybridization; D-FISH, dual-fusion FISH; ALCL, anaplastic large cell lymphoma; ALK–, anaplastic lymphoma kinase-negative; cALCL, cutaneous ALCL; PTCL, NOS, peripheral T-cell lymphoma, not otherwise specified; Hyb. fail., hybridization failure
†Index case (sequenced)
*As determined using Probes #3 and #4
**1R2F signal pattern with BAP probe; D-FISH results confirmed translocation
***Cases 14 and 15 were different tumors from the same patient To determine the incidence of FLJ43663 rearrangements in the absence of 6p25.3 translocations, FISH was performed using the 7q32.3 BAP probe on tissue microarrays (TMAs), constructed as described elsewhere (Feldman et al., Am. J. Clin. Pathol., 130:178-185 (2008) and Feldman et al., Leukemia, 22:1139-1143 (2008)). TCLs from 143 patients were tested. Hybridization was successful in 110 and failed in 33. Of the 110 patients with successful hybridizations, only 1 (<1%) exhibited rearrangement of FLJ43663. This case was an ALK-negative ALCL (1 of 11 ALK-negative ALCLs with successful hybridizations). An additional 7 TCLs had extra copies of the FLJ43663 locus. These data are summarized in Table 7. Taken together, these results suggest that translocations of FLJ43663 are rare in the absence of 6p25.3 rearrangements, and, to date, are only seen in ALK-negative ALCLs (systemic or cutaneous).

TABLE 7

Abnormalities of the FLJ43663 locus on 7q32.3 in patients lacking 6p25.3 rearrangements

|                     | ALCL, ALK− | ALCL, ALK+ | cALCL | PTCL, NOS | AITL | NKTL | Other** | Total |
|---------------------|------------|------------|-------|-----------|------|------|---------|-------|
| Rearranged          | 1          | 0          | 0     | 0         | 0    | 0    | 0       | 1     |
| Additional Copies*  | 0          | 1          | 0     | 4         | 0    | 2    | 0       | 7     |
| Normal              | 10         | 10         | 2     | 43        | 20   | 5    | 12      | 102   |
| Failed Hybridization| 6          | 2          | 1     | 15        | 4    | 2    | 3       | 33    |
| Total               | 17         | 13         | 3     | 62        | 24   | 9    | 15      | 143   |

Abbreviations: ALCL, anaplastic large cell lymphoma; ALK, anaplastic lymphoma kinase; cALCL, primary cutaneous ALCL; PTCL, NOS, peripheral T-cell lymphoma, not otherwise specified; AITL, angioimmunoblastic T-cell lymphoma; NKTL, extranodal NK/T-cell lymphoma, nasal type.
*Additional copies defined as 4 or more fusion signals
**Enteropathy associated TCL (2), hepatosplenic TCL (2), subcutaneous panniculitis-like TCL (2), mycosis fungoides (4), cutaneous CD4+ small/medium TCL (1), large granular lymphocyte leukemia (4)

Figure 20:
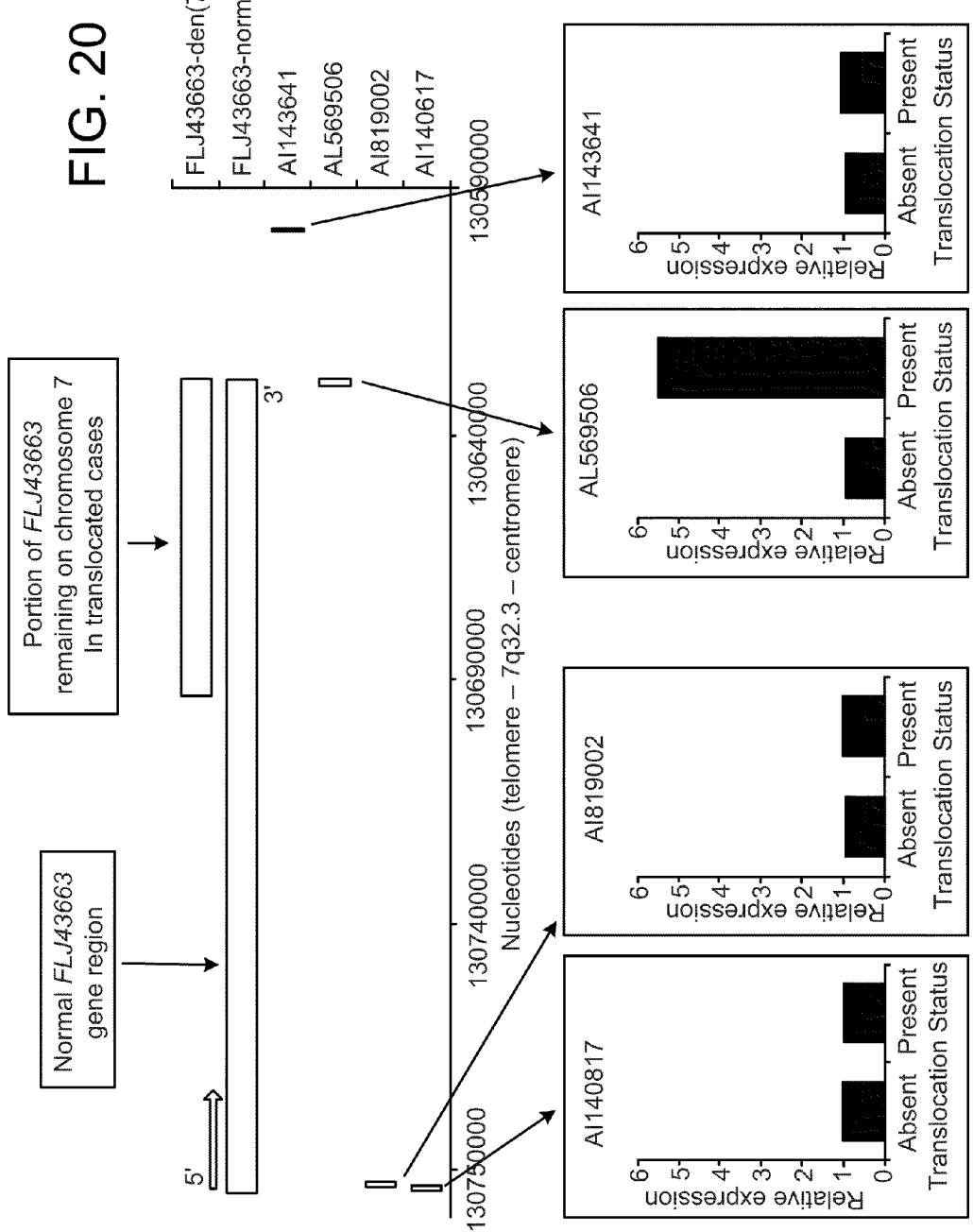
FIG. 20. Expression of the 3' terminus of FLJ43663 on 7p32.3 is increased in T-cell lymphomas with 6p25.3 rearrangements. Gene microarray data from 25 TCL patients shows expression of FLJ43663 in 21 untranslocated cases and 4 translocated cases. The panel above shows the relative locations of the normal FLJ43663 locus and the 3' portion remaining on the derivative chromosome 7 after translocation in the sequenced case. The relative locations of 4 EST-based array probes are shown. The bottom panels show mean relative expression values normalized to the mean expression in untranslocated cases. Translocated cases showed a mean expression value of the 3' EST (AL569506) 5.5-fold higher than that seen in untranslocated cases, whereas there was no difference in expression of 5' probes or a 3' probe outside the FLJ43663 locus.

To determine the effect of 6p25.3 rearrangements on expression of genes near the sequenced breakpoint on 7q32.3, a gene expression microarray analysis (Affymetrix U133 plus 2.0) was performed on 25 cases of TCLs, including 4 with and 21 without 6p25.3 rearrangements. The expression probe on 7q32.3 most up-regulated among the translocated cases was derived from the EST AL569506, which resides within the 3′ terminus of FLJ43663 itself (FIG. 20). This region exhibited 5.5-fold overexpression in translocated cases compared to non-translocated cases. This 3′ region of FLJ43663 was the region remaining on the der(7) after the t(6; 7)(p25.3; q32.3) translocation. Probes at the 5′ end of FLJ43663, as well as a probe farther 3′ (centromeric) to FLJ43663, exhibited no evidence of overexpression.

Figure 21:
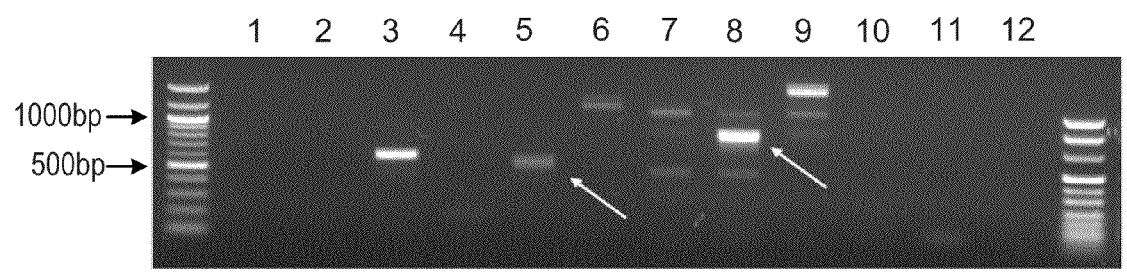
FIG. 21. An FLJ43663/DUSP22 fusion transcript is present in the sequenced case with t(6; 7)(p25.3; q32.3). PCR was performed on cDNA using primers to FLJ43663 and DUSP22 (100 by ladder). The arrows indicate bands demonstrating fusion transcripts of the predicted sizes. The band in lane 5 was generated using primers CCCTGGGGCATTT-TATTAA (SEQ ID NO:1) and AGCCACTGCCGATACT-GATG (SEQ ID NO:2) (566 bp), and that indicated in lane 8 was generated using primers GCAGCCTGGCGTGACAAG (SEQ ID NO:3) and AGCCACTGCCGATACTGATG (SEQ ID NO:4) (842 bp). These primers generate no matches by in silico PCR of the normal human genome, 22 and are ~100 kb apart in the hybrid genomic DNA from the sequenced patient. The bright bands in lanes 3 and 9 represent amplicons of the expected sizes using primers for the intact regions (not incorporating the breakpoint) of DUSP22 (lane 3) and FLJ43663 (lane 9), respectively. Sequencing of the band shown in lane 5 confirms the presence of the fusion transcript, shown below, joining the 3' portion of exon 3 of FLJ43663 to the 5' portion of exon 2 of DUSP22.

FLJ43663 is a hypothetical gene region, with known transcript isoforms and a hypothetical but unproved protein product. To evaluate the sequenced case for the presence of a fusion transcript, primers from DUSP22 and FLJ43663 were utilized in a PCR reaction of cDNA prepared from DNase-treated RNA. This produced bands of the sizes predicted, indicating the presence of a fusion transcript (FIG. 21). Based on the overexpression of the 3′ terminus of FLJ43663 mRNA, and the presence of a fusion transcript, FLJ43663 appears to be aberrantly up-regulated by the t(6; 7)(p25.3; q32.3) in TCLs, and appears to contribute to the pathogenesis and/or clinical behavior of these tumors. Thus, in addition to the clinical use of detecting FLJ43663 gene rearrangements as a diagnostic/prognostic biomarker, FLJ43663, its mRNA, or its polypeptide product can be a therapeutic target in TCLs, for example, by down-regulating it. Thus, human malignancies may be targeted by reducing FLJ43663 expression.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing a lymphoma of a mammal, wherein said method comprises:
   (a) performing breakapart fluorescence in situ hybridization using a first probe that hybridizes to a 6p25.3 chromosome region and a second probe that hybridizes to a 6p25.3 chromosome region to detect a DUSP22 translocation within said lymphoma, wherein said first and second probes comprise different fluorescent signals, and
   (b) classifying said mammal as having anaplastic large-cell lymphoma.

2. The method of claim 1, wherein said mammal is a human.

3. The method of claim 1, wherein said method comprises classifying said mammal as having cutaneous anaplastic large-cell lymphoma.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctggggca ttttattaa                                                        19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agccactgcc gatactgatg                                                       20

<210> SEQ ID NO 3

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagcctggc gtgacaag                                                  18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccactgcc gatactgatg                                                20

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagccccaaa tgccttcttt ggttttctta ga                                  32

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agggcctggg tggtcttgat tttgtatttt aggaaccaga caagtacctt tttacgggtc    60
tttgaatggt                                                           70
```